United States Patent
Shibata et al.

(10) Patent No.: US 12,264,290 B2
(45) Date of Patent: Apr. 1, 2025

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Natsumi Shibata, Ichihara (JP); Naoya Fukumoto, Ichihara (JP); Tsuyoshi Kato, Ichihara (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 18/009,221

(22) PCT Filed: Jun. 7, 2021

(86) PCT No.: PCT/JP2021/021558
§ 371 (c)(1),
(2) Date: Dec. 8, 2022

(87) PCT Pub. No.: WO2021/251335
PCT Pub. Date: Dec. 16, 2021

(65) Prior Publication Data
US 2023/0242829 A1    Aug. 3, 2023

(30) Foreign Application Priority Data
Jun. 11, 2020    (JP) .................. 2020-101574

(51) Int. Cl.
*C10M 107/38*    (2006.01)
*C07C 43/13*    (2006.01)
(Continued)

(52) U.S. Cl.
CPC ......... *C10M 107/38* (2013.01); *C07C 43/137* (2013.01); *C08G 65/226* (2013.01);
(Continued)

(58) Field of Classification Search
CPC .... G11B 5/725; G11B 5/7257; C10M 107/38; C10M 2213/043; C10M 2213/04;
(Continued)

(56) References Cited

U.S. PATENT DOCUMENTS 8,518,564 B2    8/2013    Burns et al.
8,734,966 B2    5/2014    Sagata et al.
(Continued)

FOREIGN PATENT DOCUMENTS

CN    101868521 A    10/2010
CN    102320992 A    1/2012
(Continued)

OTHER PUBLICATIONS

International Search Report for PCT/JP2021/021558 dated Aug. 3, 2021 (PCT/ISA/210).
(Continued)

*Primary Examiner* — Holly Rickman
(74) *Attorney, Agent, or Firm* — Sughrue Mion, PLLC

(57) ABSTRACT

What is provided is a fluorine-containing ether compound represented by the following formula.

$$R^1-CH_2-R^2-CH_2-OCH_2CH(OH)CH_2O-CH_2-R^3-CH_2-R^4$$

(In the formula, $R^2$ and $R^3$ are perfluoropolyether chains, and $R^1$ and $R^4$ are terminal groups having two or three polar groups, in which individual polar groups are bound to different carbon atoms and the carbon atoms to which the polar groups are bound are bound to each other via a linking group having a carbon atom to which the polar groups are not bound).

10 Claims, 1 Drawing Sheet

(51) Int. Cl.
*C08G 65/22* (2006.01)
*C08G 65/331* (2006.01)
*G11B 5/725* (2006.01)
*C10N 40/18* (2006.01)

(52) U.S. Cl.
CPC ........ *C08G 65/3318* (2013.01); *G11B 5/7257* (2020.08); *C10M 2213/043* (2013.01); *C10N 2040/18* (2013.01)

(58) Field of Classification Search
CPC ... C10M 2211/0425; C10M 2211/0406; C07C 43/137; C08G 65/226; C08G 65/3318; C08G 65/007; C08G 65/331; C10N 2040/18; C10N 2030/12; C10N 2030/26
See application file for complete search history.

(56) References Cited

U.S. PATENT DOCUMENTS

| | | | | |
|---|---|---|---|---|
| 9,805,755 | B1* | 10/2017 | Yang | C10M 107/38 |
| 11,279,664 | B2* | 3/2022 | Yagyu | C07C 43/23 |
| 11,292,979 | B2* | 4/2022 | Yamaguchi | C10M 107/38 |
| 11,332,656 | B2* | 5/2022 | Al-Yami | C09K 8/50 |
| 11,820,742 | B2* | 11/2023 | Fukumoto | C08G 65/3348 |
| 2010/0233513 | A1 | 9/2010 | Imai et al. | |
| 2012/0251873 | A1 | 10/2012 | Miyawaki et al. | |
| 2015/0235664 | A1 | 8/2015 | Deng et al. | |
| 2017/0260472 | A1 | 9/2017 | Sagata et al. | |
| 2017/0337945 | A1 | 11/2017 | Nakamura et al. | |
| 2018/0127543 | A1 | 5/2018 | Watanabe et al. | |
| 2019/0237101 | A1* | 8/2019 | Lu | C08L 71/02 |
| 2019/0352573 | A1 | 11/2019 | Hatta et al. | |
| 2019/0382675 | A1 | 12/2019 | Fukumoto et al. | |
| 2019/0382676 | A1 | 12/2019 | Yamaguchi et al. | |
| 2020/0002640 | A1 | 1/2020 | Lu et al. | |
| 2020/0283392 | A1 | 9/2020 | Kato et al. | |
| 2021/0188766 | A1 | 6/2021 | Nanko et al. | |
| 2023/0120626 | A1* | 4/2023 | Fukumoto | C08G 65/333 428/833 |

FOREIGN PATENT DOCUMENTS

| | | | |
|---|---|---|---|
| CN | 102356431 A | 2/2012 | |
| CN | 108698967 A | 10/2018 | |
| EP | 3 225 612 A1 | 10/2017 | |
| JP | S47-006168 A | 4/1972 | |
| JP | H08-134036 A | 5/1996 | |
| JP | 10-143838 A | 5/1998 | |
| JP | 2009-211765 A | 9/2009 | |
| JP | 2010-143855 A | 7/2010 | |
| JP | 2010-248463 A | 11/2010 | |
| JP | 4632144 B2 | 2/2011 | |
| JP | 2011-93981 A | 5/2011 | |
| JP | 2012-7008 A | 1/2012 | |
| JP | 2012-184339 A | 9/2012 | |
| JP | 2014-509677 A | 4/2014 | |
| JP | 5786047 B2 | 9/2015 | |
| JP | 5789710 B1 | 10/2015 | |
| JP | 2018-024614 A | 2/2018 | |
| JP | 2018-076404 A | 5/2018 | |
| WO | 2012/170009 A2 | 12/2012 | |
| WO | 2013/054393 A1 | 4/2013 | |
| WO | 2015/022781 A1 | 2/2015 | |
| WO | 2015/022871 A1 | 2/2015 | |
| WO | 2016/084781 A1 | 6/2016 | |
| WO | 2016/098811 A1 | 6/2016 | |
| WO | 2017/145995 A1 | 8/2017 | |
| WO | WO-2017146995 A1 * | 8/2017 | ......... E05B 47/0004 |
| WO | WO-2017154403 A1 * | 9/2017 | ......... C07C 43/1786 |
| WO | 2018/139058 A1 | 8/2018 | |
| WO | 2018/139174 A1 | 8/2018 | |
| WO | 2018/159250 A1 | 9/2018 | |
| WO | 2019/039200 A1 | 2/2019 | |
| WO | 2019/049585 A1 | 3/2019 | |
| WO | 2019/054148 A1 | 3/2019 | |
| WO | 2019/087548 A1 | 5/2019 | |
| WO | 2021/131961 A1 | 7/2021 | |
| WO | 2021/131993 A1 | 7/2021 | |

OTHER PUBLICATIONS

X.-C. Guo, et al., "A multidentate lubricant for use in hard disk drives at sub-nanometer thickness", Journal of Applied Physics, 2012, vol. 111, pp. 024503-1 to 024503-7.
International Search Report for PCT/JP2017/006182 dated Apr. 18, 2017 [PCT/ISA/210].
First Office Action dated Nov. 16, 2020, from The China National Intellectual Property Administration in Application No. 201780012549.4.
Non-Final Office Action issued Mar. 29, 2021 in U.S. Appl. No. 15/999,837.
Non-Final Office Action issued Aug. 20, 2021 in U.S. Appl. No. 15/999,837.
International Search Report for PCT/JP2017/042189 dated Feb. 27, 2018 [PCT/ISA/210].
Non-Final Office Action issued Aug. 23, 2021 in U.S. Appl. No. 16/470,713.
Notice of Allowance issued Jan. 28, 2022 in U.S. Appl. No. 16/470,713.
Notice of Allowance issued Dec. 15, 2021 in U.S. Appl. No. 15/999,837.
International Search Report for PCT/JP2020/047070 dated Feb. 16, 2021 [PCT/ISA/210].
Non-Final Office Action dated Mar. 15, 2023 by the USPTO in U.S. Appl. No. 17/788,169.
International Search Report of PCT/JP2020/046949 dated Feb. 16, 2021 [PCT/ISA/210].
Zhang et al., "Performances of Lubricants in Hard Disk and Their Influences on Dynamic Characteristics of Magnetic Recording System", Acta Tribology, 2004, vol. 24, No. 5, pp. 476-482 (7 pages total).
Non-Final Office Action dated Nov. 8, 2023 issued by USPTO in U.S. Appl. No. 17/788,125.
Notice of Allowance dated Jul. 12, 2023 issued by USPTO in U.S. Appl. No. 17/788,169.

* cited by examiner

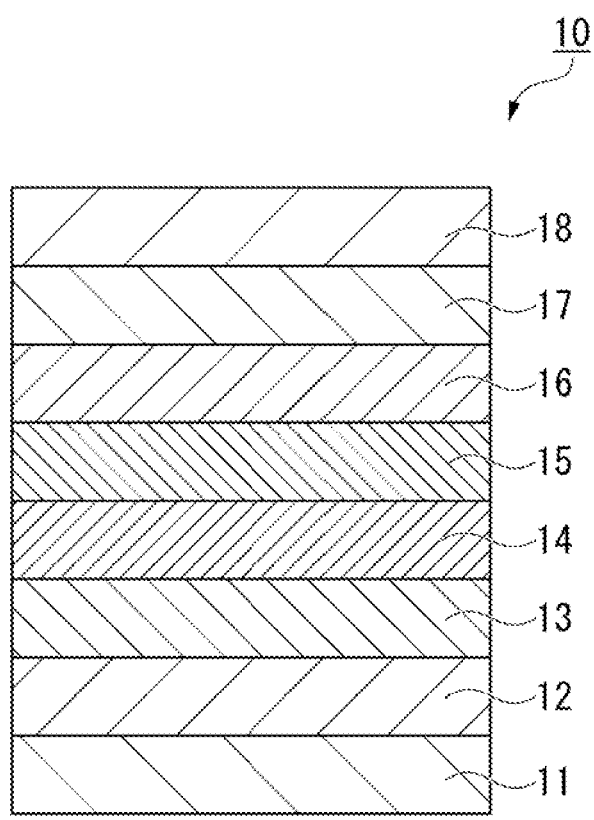

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2021/021558 filed Jun. 7, 2021, claiming priority based on Japanese Patent Application No. 2020-101574 filed Jun. 11, 2020.

TECHNICAL FIELD

The present invention relates to a fluorine-containing ether compound, a lubricant for a magnetic recording medium, and a magnetic recording medium.

Priority is claimed on Japanese Patent Application No. 2020-101574, filed Jun. 11, 2020, the content of which is incorporated herein by reference.

BACKGROUND ART

Development of magnetic recording media suitable for high recording densities is underway to improve the recording densities of magnetic recording/reproducing devices.

As a conventional magnetic recording medium, there is a magnetic recording medium in which a recording layer is formed on a substrate and a protective layer made of carbon or the like is formed on the recording layer. The protective layer protects information recorded in the recording layer and enhances the slidability of a magnetic head. In addition, the protective layer covers the recording layer to prevent metal contained in the recording layer from being corroded by environmental substances.

However, sufficient durability of the magnetic recording medium cannot be obtained by simply providing the protective layer on the recording layer. Therefore, a lubricant is applied to the surface of the protective layer to form a lubricating layer with a thickness of about 0.5 to 3 nm. The lubricating layer improves the durability and protective power of the protective layer and prevents contamination substances from intruding into the magnetic recording medium.

After forming the lubricating layer on the surface of the protective layer, a burnishing step may be performed to remove projections and particles present on the surface of the magnetic recording medium and improve the smoothness of the surface.

As a lubricant that is used at the time of forming a lubricating layer in a magnetic recording medium, there is, for example, a lubricant containing a fluorine-based polymer having a repeating structure containing —$CF_2$— and having a polar group such as a hydroxyl group at a terminal.

For example, Patent Document 1 discloses a magnetic disk containing a lubricating layer containing a perfluoropolyether having hydroxyl groups at both terminals. In addition, Patent Document 2 and 3 disclose a compound in which perfluoropolyethers are bound to both sides of an aliphatic hydrocarbon chain containing a hydroxyl group.

CITATION LIST

Patent Document

Patent Document 1: Japanese Patent No. 5786047
Patent Document 2: U.S. Pat. No. 9,805,755
Patent Document 3: United States Patent Application, Publication No. 2020/0002640
Patent Document 4: PCT International Publication No. WO2019/054148

SUMMARY OF INVENTION

Technical Problem

There is a demand for a further decrease in the flying height of a magnetic head in magnetic recording/reproducing devices. This requires a further decrease in the thickness of protective layers and lubricating layers in magnetic recording media.

However, if the thickness of protective layers and/or lubricating layers is reduced, the corrosion resistance of magnetic recording media may become insufficient. In particular, in a case where tape burnishing is performed on the surface of a magnetic recording medium after forming a lubricating layer, the corrosion resistance of the magnetic recording medium is likely to be insufficient. For this reason, there is a demand for a lubricating layer which is highly effective in suppressing corrosion of magnetic recording media.

The present invention has been made in consideration of the above circumstances, and an object of the invention is to provide a fluorine-containing ether compound that can be used as a material for a lubricant for a magnetic recording medium with which a lubricating layer highly effective in suppressing corrosion of a magnetic recording medium can be obtained.

In addition, another object of the present invention is to provide a lubricant for a magnetic recording medium containing the fluorine-containing ether compound of the present invention.

In addition, still another object of the present invention is to provide a magnetic recording medium which has a lubricating layer containing the fluorine-containing ether compound of the present invention and has excellent corrosion resistance.

Solution to Problem

The present inventors have conducted extensive studies in order to solve the above-described problem.

As a result, they have found that a fluorine-containing ether compound may suffice in which a glycerin structure (—$OCH_2CH(OH)CH_2O$—) is placed in the center of a chain structure and a perfluoropolyether chain, a methylene group, and a specific terminal group having two or three polar groups are sequentially bound to both sides of the glycerin structure via a methylene group (—$CH_2$—), thus leading to realization of the present invention.

That is, the present invention relates to the following features. The present invention has a first aspect below.

[1] A fluorine-containing ether compound represented by Formula (1) below.

(1)

(In Formula (1), $R^2$ and $R^3$ are perfluoropolyether chains; and $R^1$ and $R^4$ are terminal groups having two or three polar groups, in which individual polar groups are bound to different carbon atoms and the carbon atoms to which the polar groups are bound are bound to each other via a linking group having a carbon atom to which the polar groups are not bound.)

The compound of the first aspect of the present invention preferably includes characteristics described in [2] to [8] below. Two or more of these characteristics are also preferably combined with each other.

[2] The fluorine-containing ether compound according to [1], in which, in Formula (1) above, all of the polar groups in $R^1$ and $R^4$ are hydroxyl groups.

[3] The fluorine-containing ether compound according to [1] or [2], in which, in Formula (1) above, —$CH_2$—$R^1$ and —$CH_2$—$R^4$ are represented by Formula (2) below.

—$CH_2$-[A]-[B]—OZ    (2)

(In Formula (2), [A] is represented by Formula (3) below, [B] is represented by Formula (4) below, Z is H or a group represented by Formula (5) below; [A] and [B] in Formula (2) may be exchanged with each other, and Z is the group represented by Formula (5) below in a case where [A] is directly bound to —OZ.)

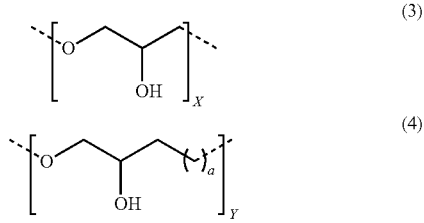

(In Formula (3), X is an integer of 0 to 2; in Formula (4), Y is an integer of 0 to 1 and a is an integer of 1 to 4; the sum of X in Formula (3) and Y in Formula (4) is 1 or 2; and b in Formula (5) is an integer of 2 to 4.)

[4] The fluorine-containing ether compound according to any one of [1] to [3], in which $R^2$ and $R^3$ in Formula (1) above are any of Formulae (6) to (8) below.

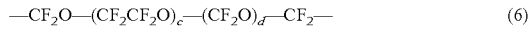
—$CF_2O$—$(CF_2CF_2O)_c$—$(CF_2O)_d$—$CF_2$—    (6)

(In Formula (6), c and d indicate an average degree of polymerization and each represent 0 to 20, provided that c or d is 0.1 or more.)

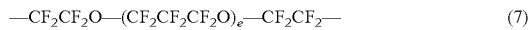
—$CF_2CF_2O$—$(CF_2CF_2CF_2O)_e$—$CF_2CF_2$—    (7)

(In Formula (7), e indicates an average degree of polymerization and represents 0.1 to 20.)

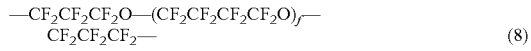
—$CF_2CF_2CF_2O$—$(CF_2CF_2CF_2CF_2O)_f$—
$CF_2CF_2CF_2$—    (8)

(In Formula (8), f indicates an average degree of polymerization and represents 0.1 to 10.)

[5] The fluorine-containing ether compound according to any one of [1] to [4], in which $R^1$ and $R^4$ in Formula (1) above each have two polar groups.

[6] The fluorine-containing ether compound according to any one of [1] to [5], in which $R^1$ and $R^4$ in Formula (1) above are the same as each other.

[7] The fluorine-containing ether compound according to any one of [1] to [6], in which $R^2$ and $R^3$ in Formula (1) above are the same as each other.

[8] The fluorine-containing ether compound according to any one of [1] to [7], in which a number average molecular weight thereof is within a range of 500 to 10,000.

A second aspect of the present invention is a lubricant below.

[9] A lubricant for a magnetic recording medium including: the fluorine-containing ether compound according to any one of [1] to [8].

A third aspect of the present invention is a magnetic recording medium below.

[10] A magnetic recording medium, in which at least a magnetic layer, a protective layer, and a lubricating layer are sequentially provided on a substrate, and the lubricating layer contains the fluorine-containing ether compound according to any one of [1] to [8].

[11] The magnetic recording medium according to [10], in which an average film thickness of the lubricating layer is 0.5 nm to 2.0 nm.

Advantageous Effects of Invention

The fluorine-containing ether compound of the present invention is the compound represented by Formula (1) above, and therefore can be used as a material for a lubricant for a magnetic recording medium with which a lubricating layer highly effective in suppressing corrosion of a magnetic recording medium can be obtained.

Since the lubricant for a magnetic recording medium of the present invention contains the fluorine-containing ether compound of the present invention, a lubricating layer highly effective in suppressing corrosion of a magnetic recording medium can be formed.

The magnetic recording medium of the present invention has the lubricating layer containing the fluorine-containing ether compound of the present invention, and therefore has excellent corrosion resistance. For this reason, the magnetic recording medium of the present invention has excellent reliability and durability. In addition, since the magnetic recording medium of the present invention has the lubricating layer highly effective in suppressing corrosion, the thickness of a protective layer and/or the lubricating layer can be reduced.

BRIEF DESCRIPTION OF DRAWINGS

The FIGURE is a schematic cross-sectional view showing one preferred embodiment of a magnetic recording medium of the present invention.

DESCRIPTION OF EMBODIMENT

Hereinafter, preferable examples of a fluorine-containing ether compound, a lubricant for a magnetic recording medium (hereinafter, abbreviated as a "lubricant" in some cases), and a magnetic recording medium of the present invention will be described in detail. The present invention is not limited to only the embodiment shown below. For example, the present invention is not limited to only the following examples. Within the scope not departing from the gist of the present invention, numbers, quantities, ratios, compositions, types, positions, materials, configurations, and the like can be added, omitted, substituted, or changed.

[Fluorine-Containing Ether Compound]

A fluorine-containing ether compound of the present embodiment is represented by Formula (1) below.

$R^1$—$CH_2$—$R^2$—$CH_2$—$OCH_2CH(OH)CH_2O$—
$CH_2$—$R^3$—$CH_2$—$R^4$    (1)

(In Formula (1), $R^2$ and $R^3$ are perfluoropolyether chains, and $R^1$ and $R^4$ are terminal groups having two or three polar groups, in which individual polar groups are bound to different carbon atoms and the carbon atoms to which the polar groups are bound are bound to each other via a linking group having a carbon atom to which the polar groups are not bound.)

In the fluorine-containing ether compound represented by Formula (1), $R^1$ and $R^4$ are each independently terminal groups having two or three polar groups. In the fluorine-containing ether compound represented by Formula (1), since $R^1$ and $R^4$ have polar groups, in a case where a lubricating layer is formed on a protective layer using a lubricant containing the fluorine-containing ether compound, a suitable interaction is generated between the lubricating layer and the protective layer.

In the fluorine-containing ether compound represented by Formula (1), the total number of polar groups in $R^1$ and polar groups in $R^4$ is 4 to 6. Since the above-described total number is 4 or more, the lubricating layer containing the fluorine-containing ether compound has high adhesiveness (adhesion properties) with respect to the protective layer. In addition, since the above-described total number is 6 or less, it is possible to prevent pickup, which is adhesion to a magnetic head as foreign matter (smears) due to excessively high polarity of the fluorine-containing ether compound, in a magnetic recording medium having the lubricating layer containing the fluorine-containing ether compound.

The number of polar groups in $R^1$ is preferably the same as the number of polar groups in $R^4$. That is, it is preferable that $R^1$ and $R^4$ each have two polar groups or each have three polar groups. In this case, since the lubricant containing the fluorine-containing ether compound adheres closely to the protective layer with a good balance, a lubricating layer with a high coating rate is likely to be obtained. In particular, in a case where $R^1$ and $R^4$ each have two polar groups, the interaction between the polar groups contained in the fluorine-containing ether compound is not excessive and imbalance of the polar groups is little, so that intramolecular aggregation is unlikely to occur. Moreover, in the case where $R^1$ and $R^4$ each have two polar groups, the hydrophilicity of the molecule is not too high, so that a fluorine-containing ether compound with moderate hydrophobicity is obtained. Therefore, the lubricating layer containing the fluorine-containing ether compound in which $R^1$ and $R^4$ each have two polar groups has excellent adhesion properties with respect to the protective layer and is highly effective in suppressing corrosion of a magnetic recording medium, which is more preferable.

The polar groups in $R^1$ and $R^4$ can be appropriately selected depending on the performance required of a lubricant containing a fluorine-containing ether compound. Examples of polar groups in $R^1$ and $R^4$ include a hydroxyl group (—OH), an amino group (—NH$_2$), a carboxy group (—COOH), an aldehyde group (—COH), a carbonyl group (—CO—), and a sulfo group (—SO$_3$H). Among these, the polar group in $R^1$ and $R^4$ is preferably a hydroxyl group. A hydroxyl group has a strong interaction with a protective layer, particularly a protective layer made of a carbon-based material. Therefore, if the polar groups in $R^1$ and/or $R^4$ are hydroxyl groups, a lubricating layer containing a fluorine-containing ether compound has high adhesiveness (adhesion properties) with respect to the protective layer. Since a lubricating layer having high adhesion properties with respect to the protective layer can be obtained, all of the two or three polar groups in $R^1$ and $R^4$ are more preferably hydroxyl groups.

Each polar group in $R^1$ and $R^4$ is bound to a different carbon atom. In $R^1$ and $R^4$, the carbon atoms to which the polar groups are bound are bound to each other via a linking group having a carbon atom to which the polar groups are not bound. For this reason, the fluorine-containing ether compound represented by Formula (1) has favorable hydrophobicity compared to a case where, for example, carbon atoms to which polar groups are bound are bound to each other. As a result, it is inferred that the lubricating layer containing the fluorine-containing ether compound represented by Formula (1) can prevent water from intruding and effectively suppress corrosion of a magnetic recording medium.

In $R^1$ and $R^4$, the linking group between the carbon atom to which the terminal polar group is bound and the carbon atom to which the polar group adjacent to the terminal polar group is bound contains a carbon atom to which polar groups are not bound, and may or may not contain an oxygen atom. In other words, the linking group between the carbon atom to which the terminal polar group is bound and the carbon atom to which the polar group adjacent to the terminal polar group is bound may or may not have an ether bond (—O—).

In $R^1$ and $R^4$, in a case where the linking group between the carbon atom to which the terminal polar group is bound and the carbon atom to which the polar group adjacent to the terminal polar group is bound contains an oxygen atom, the above-described linking group preferably has a linear structure consisting of 3 to 9 atoms including a carbon atom to which polar groups are not bound and more preferably has a linear structure consisting of 3 to 5 atoms. Even in the case where the above-described linking group contains an oxygen atom, if the linking group has a linear structure consisting of 3 or more atoms including a carbon atom to which polar groups are not bound, a fluorine-containing ether compound having favorable hydrophobicity is obtained. In addition, if the above-described linking group has a linear structure consisting of 9 or less atoms, problems are not caused in adhesion properties with respect to the protective layer due to a too hydrophobic linking group. As a result, a lubricating layer containing a fluorine-containing ether compound in which the above-described linking group has a linear structure consisting of the above-described number of atoms can have excellent adhesion properties with respect to the protective layer and can prevent water from intruding, which is highly effective in suppressing corrosion of a magnetic recording medium.

In $R^1$ and $R^4$, in a case where the linking group between the carbon atom to which the terminal polar group is bound and the carbon atom to which the polar group adjacent to the terminal polar group is bound does not contain an oxygen atom, the above-described linking group preferably has a linear structure consisting of 1 to 4 atoms including a carbon atom to which polar groups are not bound. In a case where the above-described linking group does not contain an oxygen atom but has a linear structure consisting of 1 or more atoms including a carbon atom to which polar groups are not bound, a fluorine-containing ether compound having favorable hydrophobicity is obtained. In addition, if the above-described linking group has a linear structure consisting of 4 or less atoms, problems are not caused in adhesion properties with respect to the protective layer due to a too hydrophobic linking group. As a result, a lubricating layer containing a fluorine-containing ether compound in which the above-described linking group has a linear structure consisting of the above-described number of atoms can have excellent adhesion properties with respect to the protective layer and can prevent water from intruding, which is highly effective in suppressing corrosion of a magnetic recording medium.

$R^1$ and $R^4$ may be the same as or different from each other. In a case where $R^1$ and $R^4$ are the same as each other, a fluorine-containing ether compound, which is likely to wet and spread evenly on the protective layer and from which a lubricating layer having a uniform film thickness is likely to be obtained, is obtained. As a result, the lubricating layer containing this fluorine-containing ether compound is likely to have a favorable coating rate, which is preferable. In addition, in the case where $R^1$ and $R^4$ are the same as each other, the compound can be efficiently produced through fewer production steps compared to a case where $R^1$ and $R^4$ are different from each other.

In the fluorine-containing ether compound represented by Formula (1), —$CH_2$—$R^1$ and —$CH_2$—$R^4$ are preferably represented by Formula (2) below.

—$CH_2$-[A]-[B]—OZ (2)

(In Formula (2), [A] is represented by Formula (3) below, [B] is represented by Formula (4) below, Z is H or a group represented by Formula (5) below; [A] and [B] in Formula (2) may be exchanged with each other, and Z is the group represented by Formula (5) below in a case where [A] is directly bound to —OZ.)

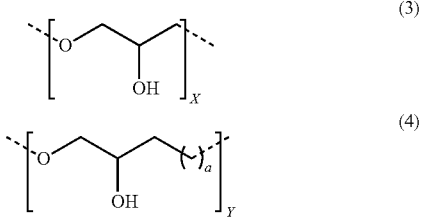

(In Formula (3), X is an integer of 0 to 2; in Formula (4), Y is an integer of 0 to 1 and a is an integer of 1 to 4; the sum of X in Formula (3) and Y in Formula (4) is 1 or 2; and b in Formula (5) is an integer of 2 to 4.)

$CH_2$—$R^1$ and —$CH_2$—$R^4$ represented by Formula (2) each may have, for example, one [A] represented by Formula (3) and one [B] represented by Formula (4), may have only one or two [A]'s, or may have only one [B]. If —$CH_2$—$R^1$ and/or —$CH_2$—$R^4$ have both [A] and [B], either [A] or [B] may be placed on the perfluoropolyether chain side. In addition, in a case where [A] is directly bound to —OZ, Z is a group represented by Formula (5).

Since —$CH_2$—$R^1$ and —$CH_2$—$R^4$ are represented by Formula (2), in a case where there are two or three hydroxyl groups in $R^1$ and/or $R^4$, the linking group between the carbon atom to which the terminal hydroxyl group is bound and the carbon atom to which the hydroxyl group adjacent to the terminal hydroxyl group is bound has a linear structure with an appropriate number of atoms. Furthermore, in a case where there are three hydroxyl groups in $R^1$ and/or $R^4$, the linking group between the carbon atom to which the hydroxyl group placed on the perfluoropolyether chain side is bound and the carbon atom to which the hydroxyl group adjacent to that hydroxyl group is bound also has a linear structure with an appropriate number of atoms. Accordingly, in the case where —$CH_2$—$R^1$ and —$CH_2$—$R^4$ are represented by Formula (2), a fluorine-containing ether compound having appropriate hydrophobicity is obtained.

In the case where [A] in Formula (2) is directly bound to —OZ, Z is the group represented by Formula (5) and is not H. For example, if Z is H in the case where [A] is directly bound to —OZ, a terminal group is obtained in which the carbon atom to which the hydroxyl group in [A] is bound is directly bound to the carbon atom to which the hydroxyl group, which is —OZ in which Z is H, is bound. For this reason, the hydrophilicity of the fluorine-containing ether compound is high. As a result, a lubricating layer containing the fluorine-containing ether compound lacks hydrophobicity, and the corrosion resistance of a magnetic recording medium on which the lubricating layer is provided becomes insufficient.

In addition, in Formula (2), X in Formula (3) is an integer of 0 to 2, Y in Formula (4) is an integer of 0 to 1, and the sum of X in Formula (3) and Y in Formula (4) is 1 or 2. For this reason, the proportion of —$CH_2$—$R^1$ and/or —$CH_2$—$R^4$ in the fluorine-containing ether compound represented by Formula (1) does not become too high. Accordingly, the proportion of perfluoropolyether chains represented by $R^2$ and $R^3$ contained in the molecule is sufficient, and a fluorine-containing ether compound with more favorable hydrophobicity is obtained.

In Formula (2), in a case where, in Formula (4), Y is 1 and a is an integer of 1 to 4, a fluorine-containing ether compound having appropriate hydrophobicity is obtained, which is preferable. In Formula (4), a is preferably an integer of 2 to 4 to obtain a fluorine-containing ether compound having more appropriate hydrophobicity.

In Formula (2), in a case where Z is Formula (5) and b is an integer of 2 to 4, a fluorine-containing ether compound having appropriate hydrophobicity is obtained, which is preferable. In a case where Z is Formula (5) and b is 2 or more, a terminal group is obtained in which the oxygen atom of the ether bond (—O—) which is bound to Z and the hydroxyl group in Formula (5) are respectively bound to different carbon atoms. As a result, due to the flexibility of the ether bond, the hydroxyl group in Formula (5) can be prevented from being close to and being aggregated with the hydroxyl group in [A] and/or [B], and the hydrophilicity of the fluorine-containing ether compound can be prevented from being too high. In addition, if b is 4 or less, problems are not caused in adhesion properties with respect to the protective layer due to a too hydrophobic linking group. b in Formula (5) above is preferably an integer of 3 to 4 to obtain a fluorine-containing ether compound having more appropriate hydrophobicity.

$R^2$ and $R^3$ in the fluorine-containing ether compound represented by Formula (1) are perfluoropolyether chains (PFPE chains). Due to the PFPE chains represented by $R^2$ and $R^3$, in a case where a lubricant containing the fluorine-containing ether compound of the present embodiment is applied onto a protective layer to form a lubricating layer, the surface of the protective layer is covered and lubricity is imparted to the lubricating layer to reduce frictional force between a magnetic head and the protective layer. In addition, since the PFPE chains have low surface energy, water resistance is imparted to the lubricating layer containing the fluorine-containing ether compound of the present embodiment and the corrosion resistance of the magnetic recording medium on which the lubricating layer is provided is improved.

$R^2$ and $R^3$ are PFPE chains and can be appropriately selected depending on the performance and the like required of a lubricant containing a fluorine-containing ether compound. Examples of PFPE chains include PFPE chains consisting of a perfluoromethylene oxide polymer, a perfluoroethylene oxide polymer, a perfluoro-n-propylene oxide polymer, a perfluoroisopropylene oxide polymer, and copolymers thereof.

Specifically, $R^2$ and $R^3$ in Formula (1) are preferably any of Formulae (6) to (8) below. The arrangement sequence of ($CF_2CF_2O$) and ($CF_2O$) which are repeating units in Formula (6) is not particularly limited. Formula (6) may include any of a random copolymer, a block copolymer, and an alternating copolymer composed of the monomer units $(CF_2-CF_2-O)$ and $(CF_2-O)$.

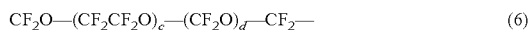
$$CF_2O-(CF_2CF_2O)_c-(CF_2O)_d-CF_2- \quad (6)$$

(In Formula (6), c and d indicate an average degree of polymerization and each represent 0 to 20, provided that c or d is 0.1 or more.)

$$-CF_2CF_2O-(CF_2CF_2CF_2O)_e-CF_2CF_2- \quad (7)$$

(In Formula (7), e indicates an average degree of polymerization and represents 0.1 to 20.)

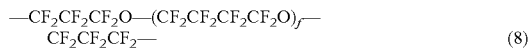
$$-CF_2CF_2CF_2O-(CF_2CF_2CF_2CF_2O)_f-CF_2CF_2CF_2- \quad (8)$$

(In Formula (8), f indicates an average degree of polymerization and represents 0.1 to 10.)

c and d indicating an average degree of polymerization in Formula (6) are each 0 to 20 (provided that c or d is 0.1 or more), e indicating an average degree of polymerization in Formula (7) is 0.1 to 20, and f indicating an average degree of polymerization in Formula (8) is 0.1 to 10. If c, d, e, and f are 0.1 or more, a fluorine-containing ether compound, from which a lubricating layer having favorable wear resistance and capable of suppressing corrosion of a magnetic recording medium can be obtained, is obtained. In addition, if c, d, and e are each 20 or less and f is 10 or less, the viscosity of a fluorine-containing ether compound does not become too high, and a lubricant containing this fluorine-containing ether compound becomes easy to apply, which is preferable. All of c, d, e, and f indicating an average degree of polymerization are preferably 2 to 10 and more preferably 3 to 8 to obtain a fluorine-containing ether compound which can easily wet and spread on a protective layer and from which a lubricating layer having a uniform film thickness is likely to be obtained. c, d, and e each may be, as necessary, 0.5 to 18, 1 to 16, 3 to 14, 4 to 7, or 5 to 6. f may be, as necessary, 1 to 10, 2 to 9, 3 to 8, 3 to 6, 4 to 7, or 5 to 6.

In the case where $R^2$ and $R^3$ in Formula (1) are any of Formulae (6) to (8), a fluorine-containing ether compound is easily synthesized, which is preferable. In a case where $R^2$ and $R^3$ are Formula (6) or (7), the procurement of raw materials is easy, which is preferable.

In addition, in the case where $R^2$ and $R^3$ are any of Formulae (6) to (8), the ratio of the number of oxygen atoms (the number of ether bonds (—O—)) to the number of carbon atoms in the perfluoropolyether chain is appropriate. For this reason, a fluorine-containing ether compound with moderate hardness is obtained. Accordingly, a fluorine-containing ether compound applied onto a protective layer is less likely to be aggregated on the protective layer, and a lubricating layer having an even thinner thickness at a sufficient coating rate can be formed.

In the fluorine-containing ether compound represented by Formula (1), the PFPE chains represented by $R^2$ and $R^3$ may be the same as or different from each other. In a case where $R^2$ and $R^3$ are the same as each other, a fluorine-containing ether compound is easily synthesized, which is preferable.

Furthermore, since the fluorine-containing ether compound in which $R^2$ and $R^3$ are the same as each other and $R^1$ and $R^4$ are also the same as each other has a symmetrical structure around the glycerin structure, it is likely to wet and spread evenly on a protective layer, and a lubricating layer having a uniform film thickness is likely to be obtained, which is more preferable. In addition, the fluorine-containing ether compound in which $R^2$ and $R^3$ are the same as each other and $R^1$ and $R^4$ are also the same as each other can be produced easily and efficiently through fewer production steps.

In the fluorine-containing ether compound represented by Formula (1), the hydroxyl group (—OH) of the glycerin structure (—OCH$_2$CH(OH)CH$_2$O—) placed in the center of the chain structure improves adhesion properties with respect to a protective layer in a lubricating layer containing the fluorine-containing ether compound.

In addition, oxygen atoms placed at both end portions of the glycerin structure are bound to methylene groups (—CH$_2$—) placed on both sides of the glycerin structure to form ether bonds (—O—). These two ether bonds impart moderate flexibility to the fluorine-containing ether compound represented by Formula (1) and increase the affinity between a protective layer and the hydroxyl group in the glycerin structure.

In addition, in the fluorine-containing ether compound represented by Formula (1), perfluoropolyether chains ($R^2$ and $R^3$) are each placed between the glycerin structure placed in the center of the chain structure and the terminal groups represented by $R^1$ and $R^4$. For this reason, the distance between the hydroxyl group (—OH) in the glycerin structure and the polar groups in the terminal groups represented by $R^1$ and $R^4$ is appropriate. Therefore, both the hydroxyl group in the glycerin structure and the polar groups in the terminal groups represented by $R^1$ and $R^4$ are less likely to be inhibited from binding with active points on the protective layer due to the adjacent polar groups. Accordingly, both the hydroxyl group in the glycerin structure and the polar groups in the terminal groups represented by $R^1$ and $R^4$ are likely to participate in binding with the active points on the protective layer. In other words, all the polar groups in the above-described fluorine-containing ether compound are less likely to be polar groups that do not participate in binding with the active points on the protective layer. Accordingly, in the above-described fluorine-containing ether compound, the number of polar groups that do not participate in binding with active points on the protective layer can be reduced. As a result, the lubricating layer containing the above-described fluorine-containing ether compound has a high coating rate, which makes it difficult for environmental substances that generate contamination substances to intrude through voids, so corrosion of a magnetic recording medium can be suppressed.

In addition, in the above-described fluorine-containing ether compound, since the distance between the hydroxyl group in the glycerin structure and the polar groups in the terminal groups represented by $R^1$ and $R^4$ is appropriate, the hydroxyl group in the glycerin structure is less likely to be aggregated with the polar groups in the terminal groups represented by $R^1$ and $R^4$. Moreover, both end portions of each perfluoropolyether chain adhere closely to the protective layer due to the hydroxyl group in the glycerin structure and the polar groups in the terminal groups represented by $R^1$ and $R^4$. For this reason, the fluorine-containing ether compound applied onto the protective layer is less likely to be bulky. Accordingly, the fluorine-containing ether compound can easily wet and spread on the protective layer, and a lubricating layer having a uniform coating state is likely to be obtained. As a result, the above-described fluorine-containing ether compound can form a lubricating layer having favorable wear resistance and capable of suppressing corrosion of a magnetic recording medium.

It is preferable that the fluorine-containing ether compound represented by Formula (1) be specifically any compound represented by Formulae (1A) to (1M), (2A) to (2L), (3A) to (3L), and (4A). Since ma1 to nm1, ma2 to mm2, na1 to nm1, and na2 to nm2 in Formulae (1A) to (1M), m'a1 to m'l1 and m'a2 to m'l2 in Formulae (2A) to (2L), pa1 to pl1 and pa2 to pl2 in Formulae (3A) to (3L), and qa1 and qa2 in Formula (4A) are values indicating an average degree of polymerization, these are not necessarily integers.

In all the compounds represented by Formulae (1A) to (1L) below, $R^1$ and $R^4$ are the same as each other. In all the compounds represented by Formulae (1A) to (1M) below, $R^2$ and $R^3$ are the same as each other and are PFPE chains represented by Formula (6) above.

—$CH_2$—$R^1$ in Formulae (1A) to (1K) and (1M) are all represented by Formula (2), and the binding order of Formula (2) is represented by —$CH_2$-[A]-[B]—OZ.

In the compound represented by Formula (1A) below, X in Formula (3) is 1, Y in Formula (4) is 0, and Z is Formula (5). b in Formula (5) is 2.

In the compound represented by Formula (1B) below, X in Formula (3) is 1, Y in Formula (4) is 0, and Z is Formula (5). b in Formula (5) is 3.

In the compound represented by Formula (1C) below, X in Formula (3) is 1, Y in Formula (4) is 0, and Z is Formula (5). b in Formula (5) is 4.

In the compound represented by Formula (1D) below, X in Formula (3) is 2, Y in Formula (4) is 0, and Z is Formula (5). b in Formula (5) is 2.

In the compound represented by Formula (1E) below, X in Formula (3) is 2, Y in Formula (4) is 0, and Z is Formula (5). b in Formula (5) is 3.

In the compound represented by Formula (1F) below, X in Formula (3) is 2, Y in Formula (4) is 0, and Z is Formula (5). b in Formula (5) is 4.

In the compound represented by Formula (1G) below, X in Formula (3) is 0, Y and a in Formula (4) are each 1, and Z is a hydrogen atom.

In the compound represented by Formula (1H) below, X in Formula (3) is 0, Y and a in Formula (4) are respectively 1 and 2, and Z is a hydrogen atom.

In the compound represented by Formula (1I) below, X in Formula (3) is 0, Y and a in Formula (4) are respectively 1 and 4, and Z is a hydrogen atom.

In the compound represented by Formula (1J) below, X in Formula (3) is 1, Y and a in Formula (4) are each 1, and Z is a hydrogen atom.

In the compound represented by Formula (1K) below, X in Formula (3) is 0, Y and a in Formula (4) are each 1, and Z is Formula (5). b in Formula (5) is 3.

In the compound represented by Formula (1L) below, —$CH_2$—$R^1$ is a group represented by Formula (2), and the binding order of Formula (2) is represented by —$CH_2$—[B]-[A]-OZ. X in Formula (3) is 1, Y and a in Formula (4) are respectively 1 and 2, and Z is Formula (5). b in Formula (5) is 2.

In the compound represented by Formula (1M) below, —$CH_2$—$R^1$ is a group represented by Formula (2), X in Formula (3) is 1, Y in Formula (4) is 0, Z is Formula (5), and b in Formula (5) is 2. —$CH_2$—$R^4$ is a group represented by Formula (2), X in Formula (3) is 0, Y and a in Formula (4) are respectively 1 and 2, and Z is H.

In all the compounds represented by Formulae (2A) to (2L) below, $R^1$ and $R^4$ are the same as each other. In all the compounds represented by Formulae (2A) to (2L) below, $R^2$ and $R^3$ are the same as each other, are Formula (6) above, and are PFPE chains in which d in Formula (6) above is represented by 0.

—$CH_2$—$R^1$ in Formulae (2A) to (2K) are all represented by Formula (2), and the binding order of Formula (2) is represented by —$CH_2$-[A]-[B]—OZ.

In the compound represented by Formula (2A) below, X in Formula (3) is 1, Y in Formula (4) is 0, and Z is Formula (5). b in Formula (5) is 2.

In the compound represented by Formula (2B) below, X in Formula (3) is 1, Y in Formula (4) is 0, and Z is Formula (5). b in Formula (5) is 3.

In the compound represented by Formula (2C) below, X in Formula (3) is 1, Y in Formula (4) is 0, and Z is Formula (5). b in Formula (5) is 4.

In the compound represented by Formula (2D) below, X in Formula (3) is 2, Y in Formula (4) is 0, and Z is Formula (5). b in Formula (5) is 2.

In the compound represented by Formula (2E) below, X in Formula (3) is 2, Y in Formula (4) is 0, and Z is Formula (5). b in Formula (5) is 3.

In the compound represented by Formula (2F) below, X in Formula (3) is 2, Y in Formula (4) is 0, and Z is Formula (5). b in Formula (5) is 4.

In the compound represented by Formula (2G) below, X in Formula (3) is 0, Y and a in Formula (4) are each 1, and Z is a hydrogen atom.

In the compound represented by Formula (2H) below, X in Formula (3) is 0, Y and a in Formula (4) are respectively 1 and 2, and Z is a hydrogen atom. In the compound represented by Formula (21) below, X in Formula (3) is 0, Y and a in Formula (4) are respectively 1 and 4, and Z is a hydrogen atom.

In the compound represented by Formula (2J) below, X in Formula (3) is 1, Y and a in Formula (4) are each 1, and Z is a hydrogen atom.

In the compound represented by Formula (2K) below, X in Formula (3) is 0, Y and a in Formula (4) are each 1, and Z is Formula (5). b in Formula (5) is 3.

In the compound represented by Formula (2L) below, —$CH_2$—$R^1$ is a group represented by Formula (2), and the binding order of Formula (2) is represented by —$CH_2$—[B]-[A]-OZ. X in Formula (3) is 1, Y and a in Formula (4) are respectively 1 and 2, and Z is Formula (5). b in Formula (5) is 2.

In all the compounds represented by Formulae (3A) to (3L) below, $R^1$ and $R^4$ are the same as each other. In all the compounds represented by Formulae (3A) to (3L) below, $R^2$ and $R^3$ are the same as each other and are PFPE chains represented by Formula (7) above.

—$CH_2$—$R^1$ in Formulae (3A) to (3K) are all represented by Formula (2), and the binding order of Formula (2) is represented by —$CH_2$-[A]-[B]—OZ.

In the compound represented by Formula (3A) below, X in Formula (3) is 1, Y in Formula (4) is 0, and Z is Formula (5). b in Formula (5) is 2.

In the compound represented by Formula (3B) below, X in Formula (3) is 1, Y in Formula (4) is 0, and Z is Formula (5). b in Formula (5) is 3.

In the compound represented by Formula (3C) below, X in Formula (3) is 1, Y in Formula (4) is 0, and Z is Formula (5). b in Formula (5) is 4.

In the compound represented by Formula (3D) below, X in Formula (3) is 2, Y in Formula (4) is 0, and Z is Formula (5). b in Formula (5) is 2.

In the compound represented by Formula (3E) below, X in Formula (3) is 2, Y in Formula (4) is 0, and Z is Formula (5). b in Formula (5) is 3.

In the compound represented by Formula (3F) below, X in Formula (3) is 2, Y in Formula (4) is 0, and Z is Formula (5). b in Formula (5) is 4.

In the compound represented by Formula (3G) below, X in Formula (3) is 0, Y and a in Formula (4) are each 1, and Z is a hydrogen atom.

In the compound represented by Formula (3H) below, X in Formula (3) is 0, Y and a in Formula (4) are respectively 1 and 2, and Z is a hydrogen atom.

In the compound represented by Formula (3I) below, X in Formula (3) is 0, Y and a in Formula (4) are respectively 1 and 4, and Z is a hydrogen atom.

In the compound represented by Formula (3J) below, X in Formula (3) is 1, Y and a in Formula (4) are each 1, and Z is a hydrogen atom.

In the compound represented by Formula (3K) below, X in Formula (3) is 0, Y and a in Formula (4) are each 1, and Z is Formula (5). b in Formula (5) is 3.

In the compound represented by Formula (3L) below, —$CH_2$—$R^1$ is a group represented by Formula (2), and the binding order of Formula (2) is represented by —$CH_2$—[B]-[A]-OZ. X in Formula (3) is 1, Y and a in Formula (4) are respectively 1 and 2, and Z is Formula (5). b in Formula (5) is 2.

In the compound represented by Formula (4A) below, $R^1$ and $R^4$ are the same as each other, and $R^2$ and $R^3$ are the same as each other and are PFPE chains represented by Formula (8) above.

In the compound represented by Formula (4A) below, —$CH_2$—$R^1$ is a group represented by Formula (2), and the binding order of Formula (2) is represented by —$CH_2$-[A]-[B]—OZ. X in Formula (3) is 1, Y in Formula (4) is 0, and Z is Formula (5). b in Formula (5) is 2.

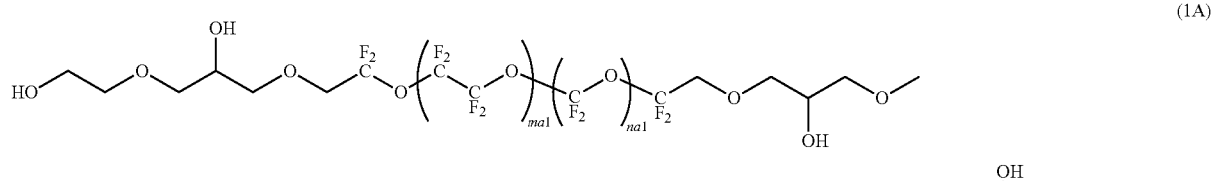

(1A)

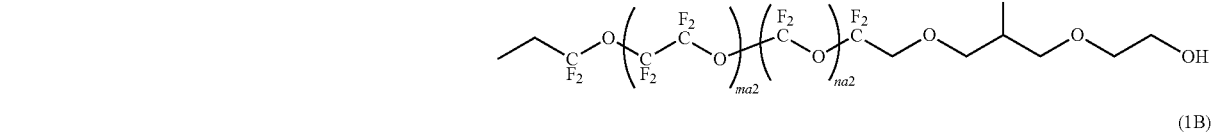

(1B)

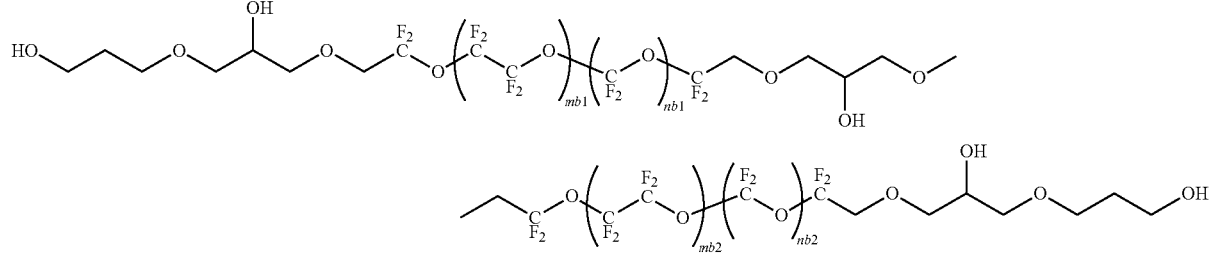

(1C)

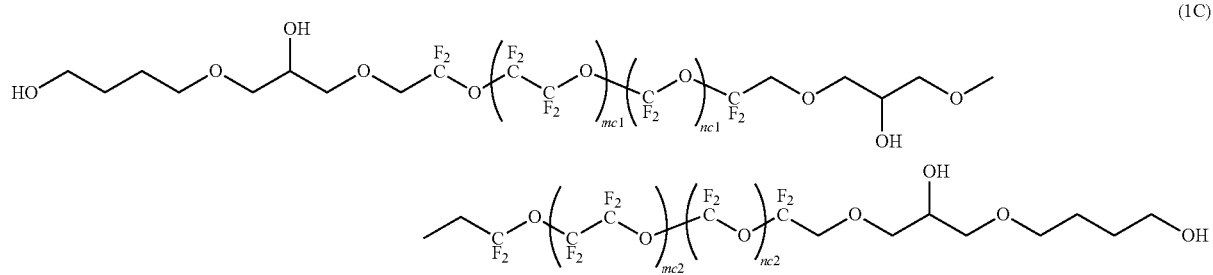

(In Formula (1A), ma1, ma2, na1, and na2 indicate an average degree of polymerization, ma1 and ma2 represent 0.1 to 20, and na1 and na2 represent 0.1 to 20.)

(In Formula (1B), nb1, mb2, nb1, and nb2 indicate an average degree of polymerization, mb1 and mb2 represent 0.1 to 20, and nb1 and nb2 represent 0.1 to 20.)

(In Formula (1C), mc1, mc2, nc1, and nc2 indicate an average degree of polymerization, mc1 and mc2 represent 0.1 to 20, and nc1 and nc2 represent 0.1 to 20.)

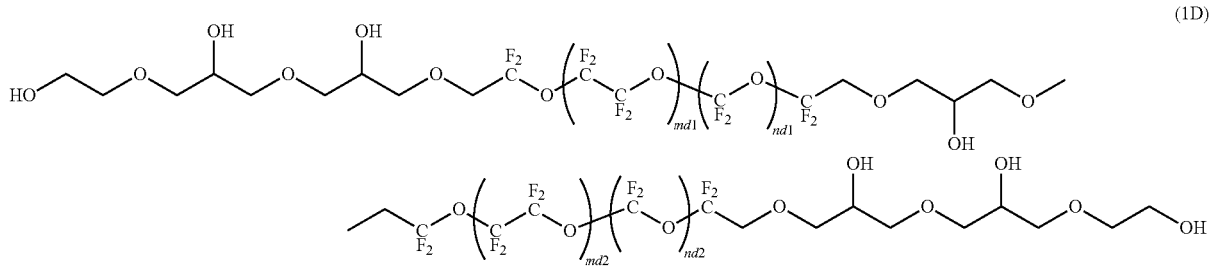
(1D)

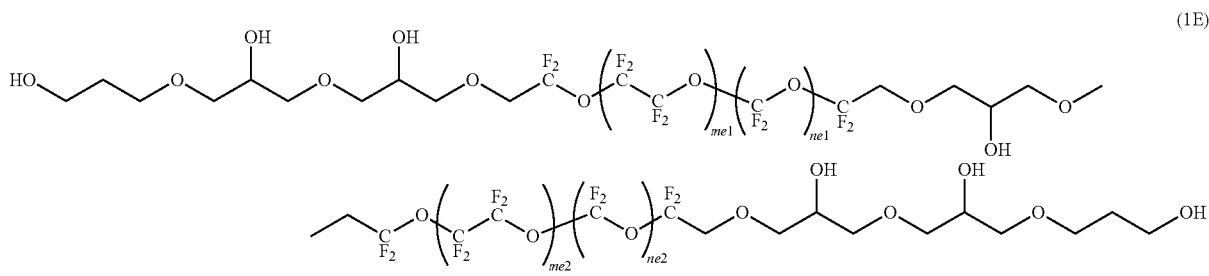
(1E)

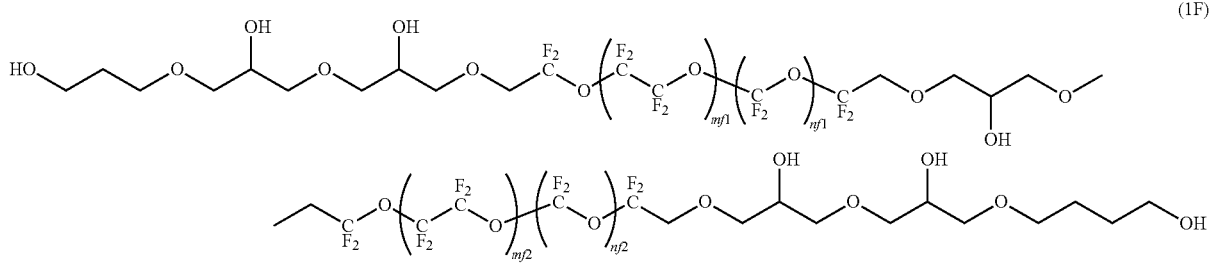
(1F)

(In Formula (1D), md1, md2, nd1, and nd2 indicate an average degree of polymerization, md1 and md2 represent 0.1 to 20, and nd1 and nd2 represent 0.1 to 20.)

(In Formula (1E), me1, me2, ne1, and ne2 indicate an average degree of polymerization, me1 and me2 represent 0.1 to 20, and ne1 and ne2 represent 0.1 to 20.)

(In Formula (1F), mf1, mf2, nf1, and nf2 indicate an average degree of polymerization, mf1 and mf2 represent 0.1 to 20, and nf1 and nf2 represent 0.1 to 20.)

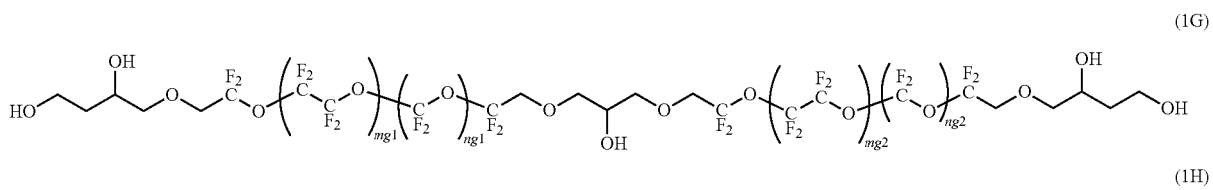
(1G)

(1H)

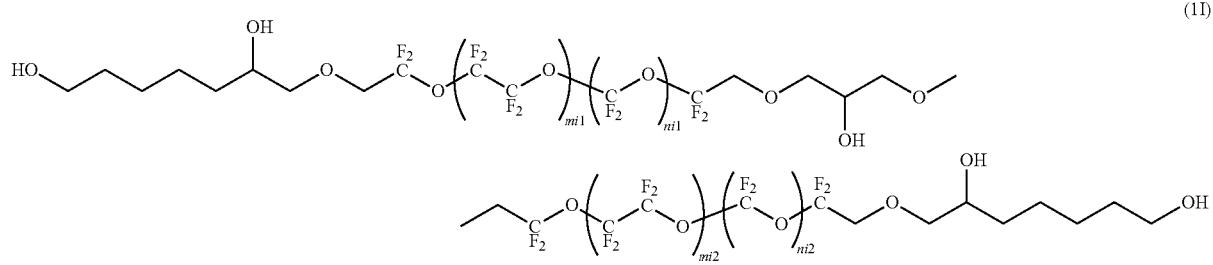
(In Formula (1G), mg1, mg2, ng1, and ng2 indicate an average degree of polymerization, mg1 and mg2 represent 0.1 to 20, and ng1 and ng2 represent 0.1 to 20.)
(In Formula (1H), mh1, mh2, nh1, and nh2 indicate an average degree of polymerization, mh1 and mh2 represent 0.1 to 20, and nh1 and nh2 represent 0.1 to 20.)
(In Formula (1I), mi1, mi2, ni1, and ni2 indicate an average degree of polymerization, mi1 and mi2 represent 0.1 to 20, and ni1 and ni2 represent 0.1 to 20.)

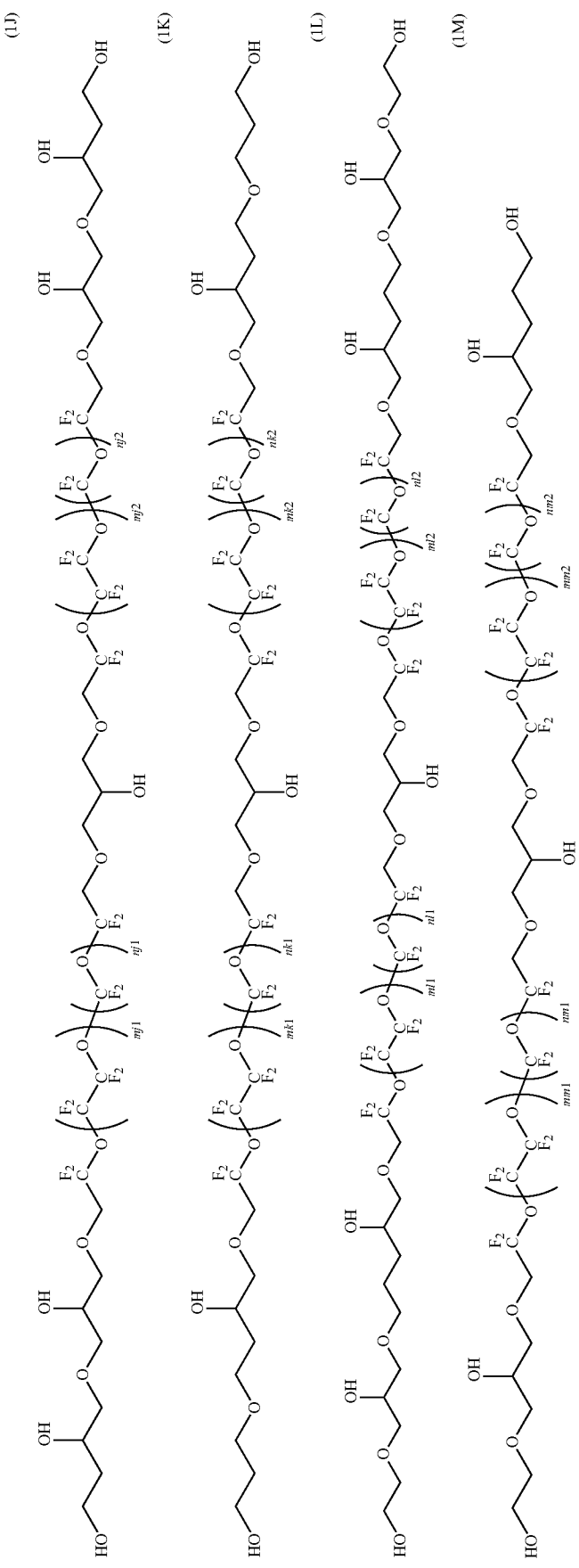

(In Formula (1J), mj1, mj2, nj1, and nj2 indicate an average degree of polymerization, mj1 and mj2 represent 0.1 to 20, and nj1 and nj2 represent 0.1 to 20.)

(In Formula (1K), mk1, mk2, nk1, and nk2 indicate an average degree of polymerization, mk1 and mk2 represent 0.1 to 20, and nk1 and nk2 represent 0.1 to 20.)

(In Formula (1L), ml1, ml2, nl1, and nl2 indicate an average degree of polymerization, ml1 and ml2 represent 0.1 to 20, and nl1 and nl2 represent 0.1 to 20.)

(In Formula (1M), mm1, mm2, nm1, and nm2 indicate an average degree of polymerization, mm1 and mm2 represent 0.1 to 20, and nm1 and nm2 represent 0.1 to 20.)

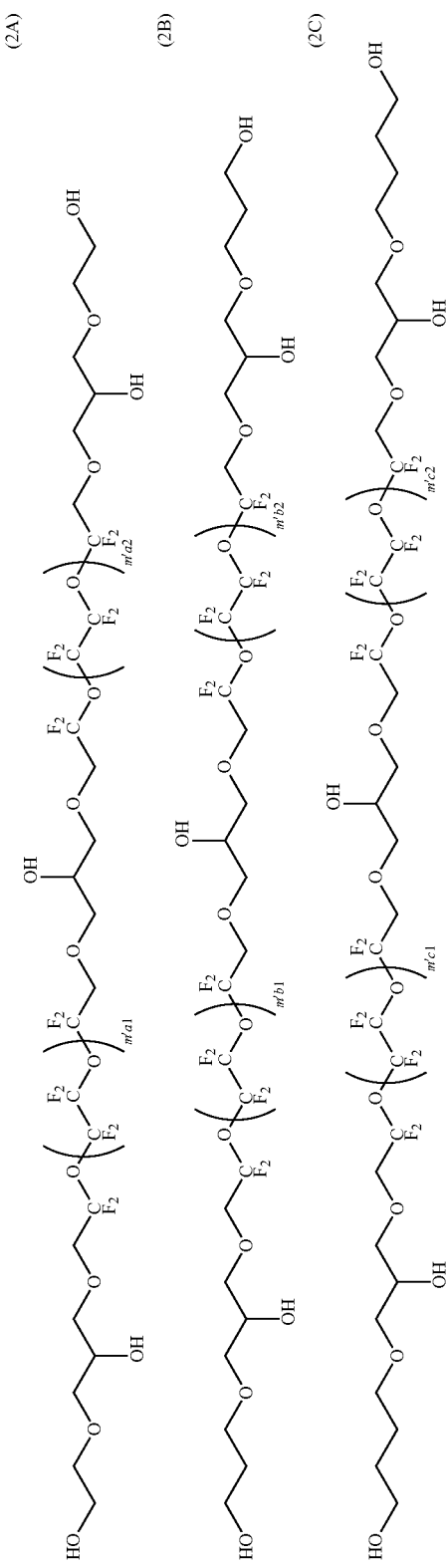

(In Formula (2A), m'a1 and m'a2 indicate an average degree of polymerization and represent 0.1 to 20.)

(In Formula (2B), m'b1 and m'b2 indicate an average degree of polymerization and represent 0.1 to 20.)

(In Formula (2C), m'c1 and m'c2 indicate an average degree of polymerization and represent 0.1 to 20.)

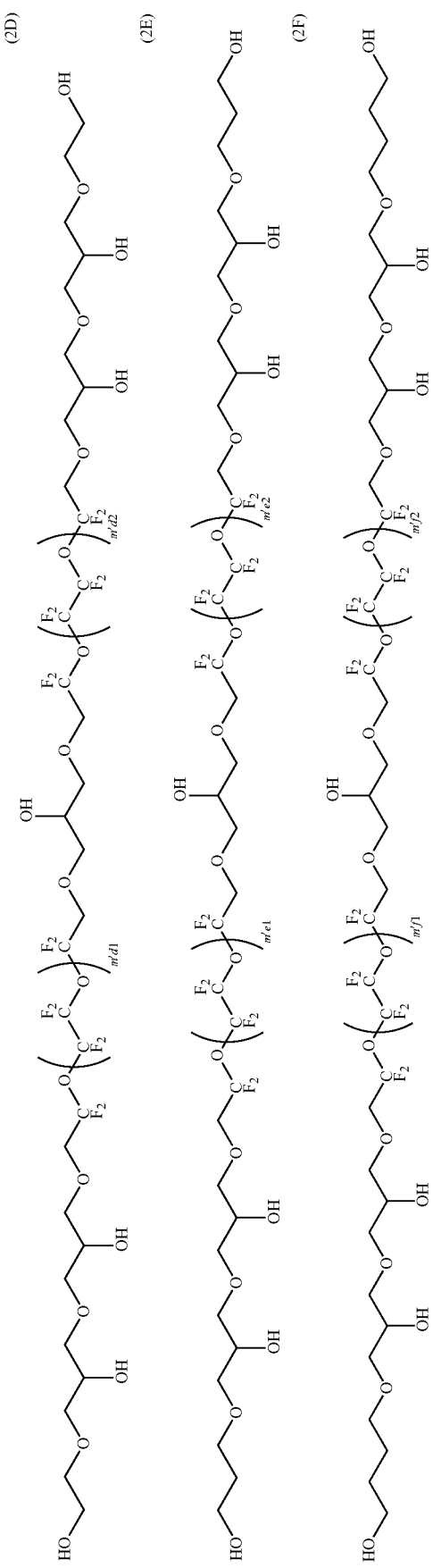

(In Formula (21)), m'd1 and m'd2 indicate an average degree of polymerization and represent 0.1 to 20.)

(In Formula (2E), m'e1 and m'e2 indicate an average degree of polymerization and represent 0.1 to 20.)

(In Formula (2F), m'f1 and m'f2 indicate an average degree of polymerization and represent 0.1 to 20.)

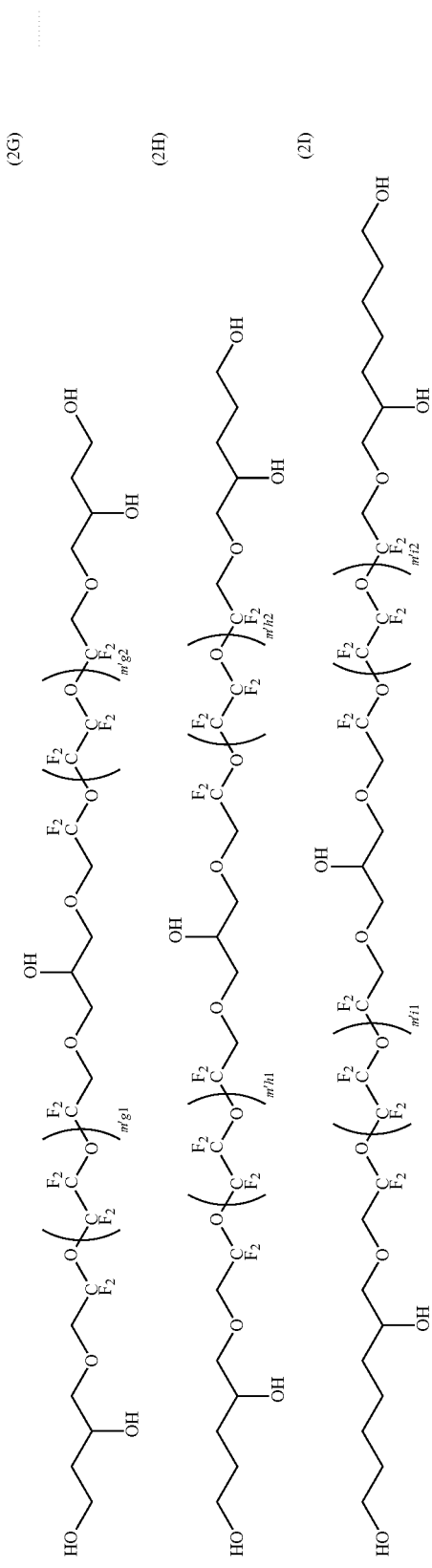

(In Formula (2G), m'g1 and m'g2 indicate an average degree of polymerization and represent 0.1 to 20.)

(In Formula (2H), m'h1 and m'h2 indicate an average degree of polymerization and represent 0.1 to 20.)

(In Formula (2I), m'i1 and m'i2 indicate an average degree of polymerization and represent 0.1 to 20.)

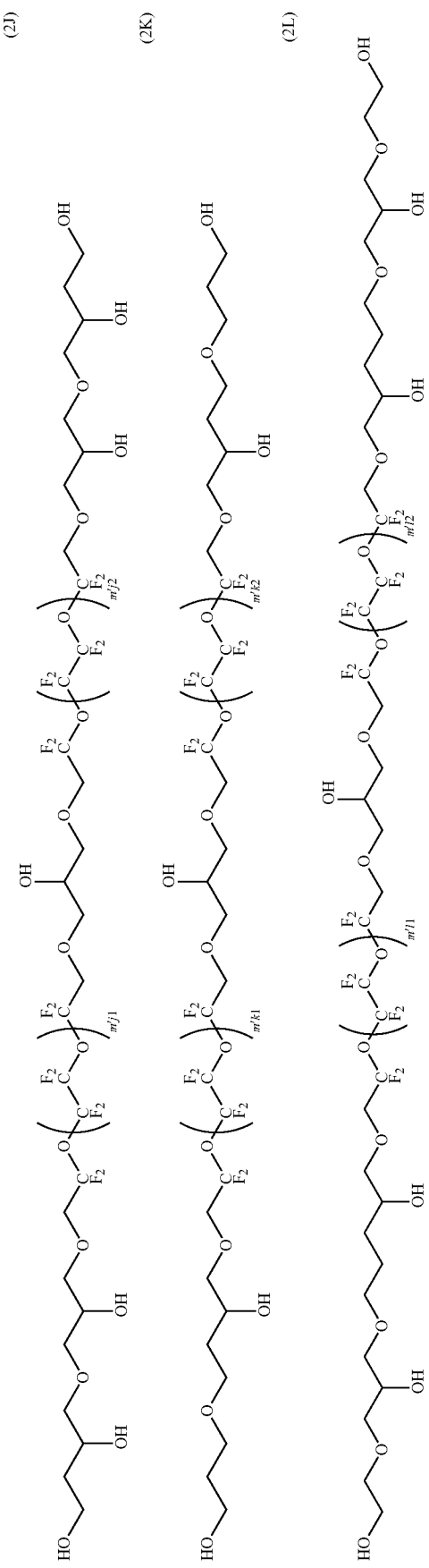

(In Formula (2J), m'j1 and m'j2 indicate an average degree of polymerization and represent 0.1 to 20.)

(In Formula (2K), m'k1 and m'k2 indicate an average degree of polymerization and represent 0.1 to 20.)

(In Formula (2L), m'l1 and m'l2 indicate an average degree of polymerization and represent 0.1 to 20.)

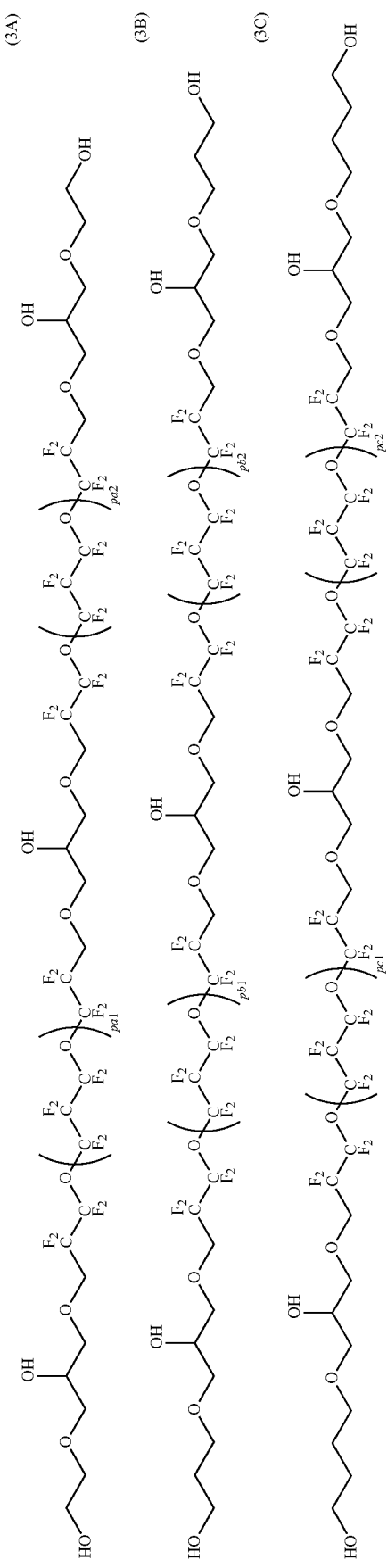

(In Formula (3A), pa1 and pa2 indicate an average degree of polymerization and represent 0.1 to 20.)

(In Formula (3B), pb1 and pb2 indicate an average degree of polymerization and represent 0.1 to 20.)

(In Formula (3C), pc1 and pc2 indicate an average degree of polymerization and represent 0.1 to 20.)

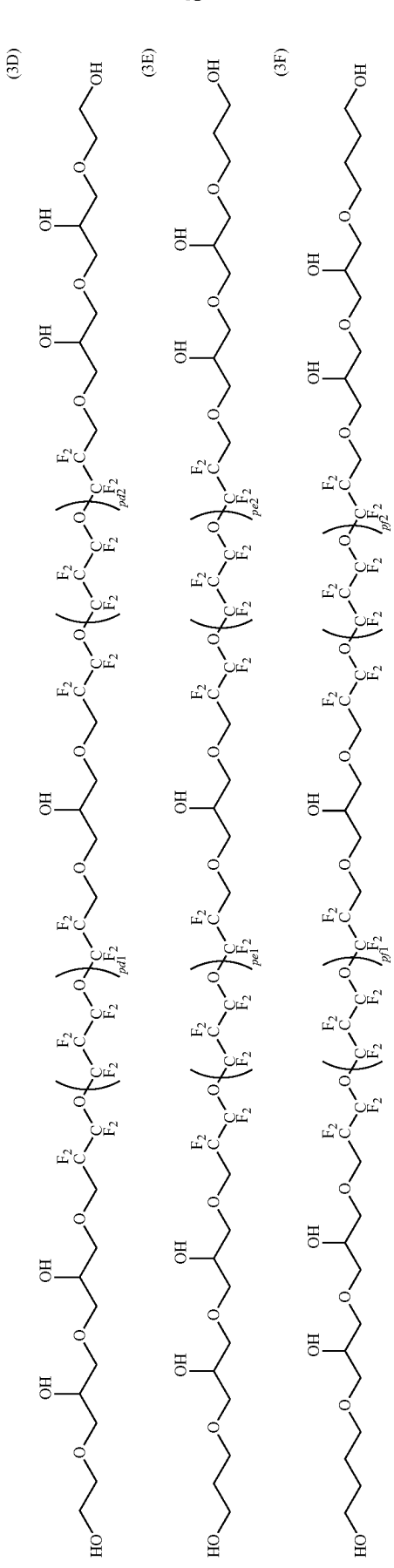

(In Formula (31)), pd1 and pd2 indicate an average degree of polymerization and represent 0.1 to 20.)

(In Formula (3E), pe1 and pe2 indicate an average degree of polymerization and represent 0.1 to 20.)

(In Formula (3F), pf1 and pf2 indicate an average degree of polymerization and represent 0.1 to 20.)

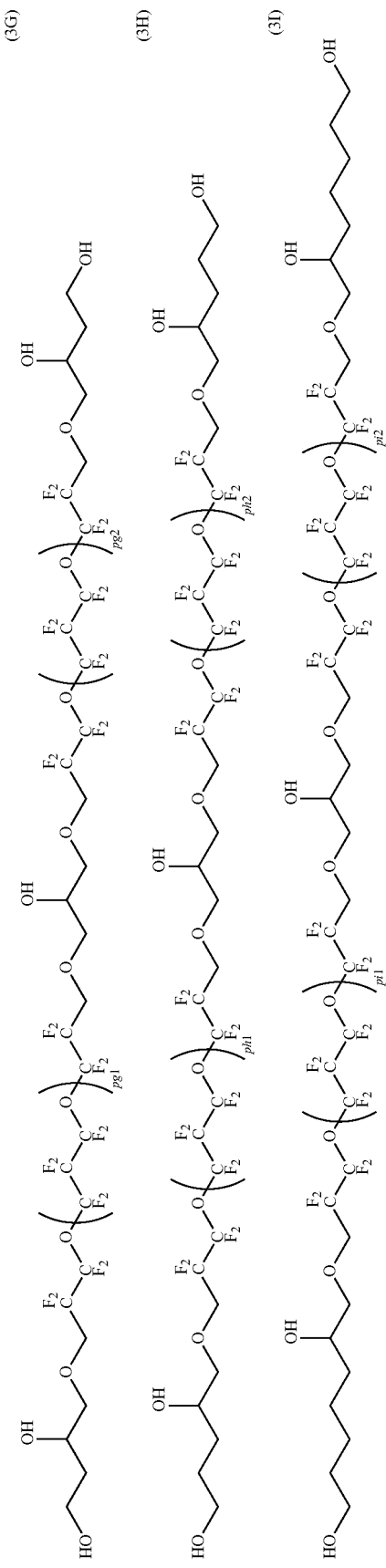

(In Formula (3G), pg1 and pg2 indicate an average degree of polymerization and represent 0.1 to 20.)

(In Formula (3H), ph1 and ph2 indicate an average degree of polymerization and represent 0.1 to 20.)

(In Formula (3I), pi1 and pi2 indicate an average degree of polymerization and represent 0.1 to 20.)

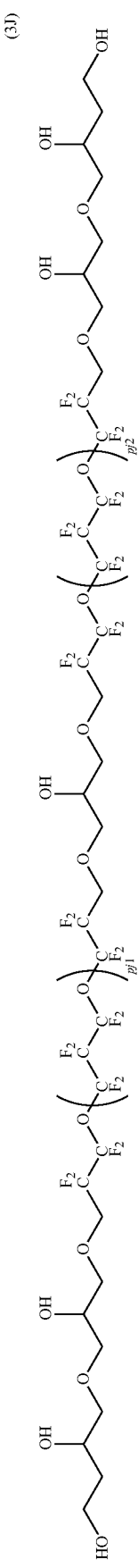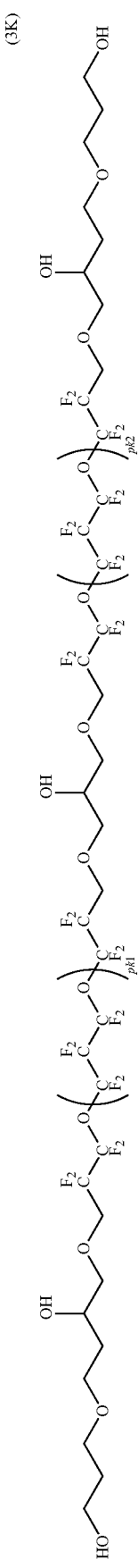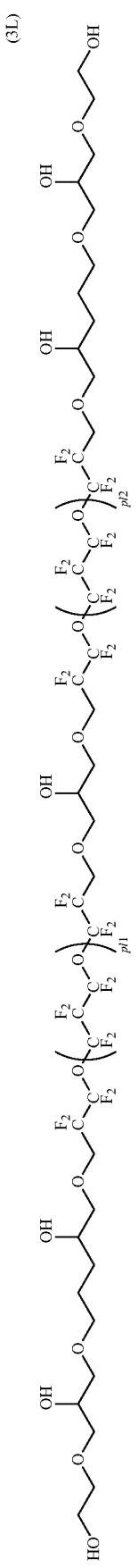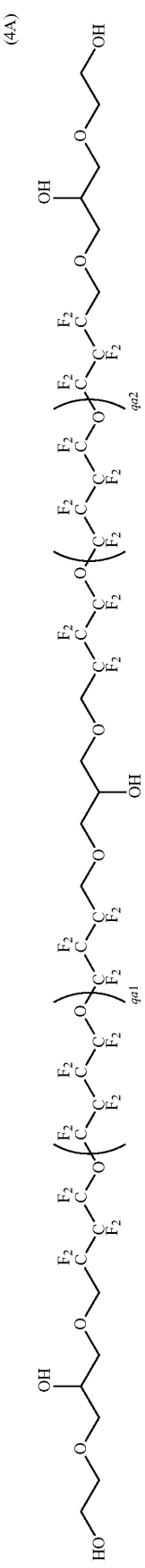

(In Formula (M), pj1 and pj2 indicate an average degree of polymerization and represent 0.1 to 20.)

(In Formula (3K), pk1 and pk2 indicate an average degree of polymerization and represent 0.1 to 20.)

(In Formula (3L), pl1 and pl2 indicate an average degree of polymerization and represent 0.1 to 20.)

(In Formula (4A), qa1 and qa2 indicate an average degree of polymerization and represent 0.1 to 10.)

If the compound represented by Formula (1) is any compound represented by Formulae (1A) to (1M), (2A) to (2L), (3A) to (3L), and (4A), the procurement of raw materials is easy and a lubricating layer capable of suppressing corrosion of a magnetic recording medium even if the lubricating layer has a thin thickness can be formed, which is preferable.

The fluorine-containing ether compound of the present embodiment can be arbitrarily selected, but the number average molecular weight (Mn) of the compound is preferably within a range of 500 to 10,000, more preferably within a range of 700 to 7,000, and particularly preferably within a range of 1,000 to 5,000. If the number average molecular weight thereof is 500 or more, a lubricant containing the fluorine-containing ether compound of the present embodiment is less likely to evaporate, whereby the lubricant can be prevented from evaporating and transferring to a magnetic head. In addition, if the number average molecular weight thereof is 10,000 or less, the fluorine-containing ether compound has an appropriate viscosity, and a thin lubricating layer can be easily formed by applying a lubricant containing this fluorine-containing ether compound. If the number average molecular weight thereof is 5,000 or less, in a case where the fluorine-containing ether compound is applied to a lubricant, the viscosity of the lubricant becomes appropriate for handling, which is more preferable. The number average molecular weight may be within a range of, for example, 1,000 to 4,500, 1,200 to 4,000, 1,400 to 3,500, 1,600 to 3,000, 1,800 to 2,800, 2,000 to 2,600, or 2,100 to 2,500.

The number average molecular weight (Mn) of the fluorine-containing ether compound is a value measured by $^1$H-NMR and $^{19}$F-NMR with AVANCE 111400 manufactured by Bruker BioSpin Group. In the nuclear magnetic resonance (NMR) measurement, a sample is diluted with a single or mixed solvent of hexafluorobenzene, acetone-d, tetrahydrofuran-d, and the like and used in the measurement. As the reference of the $^{19}$F-NMR chemical shift, the peak of hexafluorobenzene was set to −164.7 ppm. As the reference of the $^1$H-NMR chemical shift, the peak of acetone was set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method shown below.

In a case where a compound is produced in which $R^1$ and $R^4$ are the same as each other and two PFPE chains represented by $R^2$ and $R^3$ are the same as each other, a fluorine-based compound in which hydroxymethyl groups (—CH$_2$OH) are arranged at both terminals of the perfluoropolyether chain corresponding to $R^2$ (=$R^3$) in Formula (1) is first prepared. Next, the hydroxyl group of the hydroxymethyl group placed at one terminal of the fluorine-based compound is reacted with an epoxy compound having a group consisting of —$R^1$ (=—$R^4$) in Formula (1) (first reaction). As a result, an intermediate compound having a group corresponding to —$R^1$ (=—$R^4$) at one terminal of the perfluoropolyether chain corresponding to $R^2$ (=$R^3$) is obtained.

The epoxy compound having a group consisting of —$R^1$ (=—$R^4$) may be reacted with the above-described fluorine-based compound after protecting the hydroxyl group with a suitable protecting group.

Thereafter, an epoxy compound obtained by reacting the hydroxyl group of the hydroxymethyl group placed at the intermediate compound terminal with epibromohydrin is further reacted with a hydroxyl group located at a terminal of another molecule of the intermediate compound (second reaction).

By performing the above-described steps, a compound which has a glycerin structure in the center of a chain structure and in which $R^1$ and $R^4$ in Formula (1) are the same as each other and the two PFPE chains represented by $R^2$ and $R^3$ are the same as each other can be produced.

If a compound is generated in which $R^1$ is different from $R^4$ and/or two PFPE chains represented by $R^2$ and $R^3$ are different from each other, a first intermediate compound having a group corresponding to —$R^1$ at one terminal of a perfluoropolyether chain corresponding to $R^2$ is produced in the same manner as in the case of producing the compound in which $R^1$ and $R^4$ in Formula (1) above are the same as each other and the two PFPE chains represented by $R^2$ and $R^3$ are the same as each other.

Next, a second intermediate compound having a group corresponding to —$R^4$ at one terminal of a perfluoropolyether chain corresponding to $R^3$ is produced in the same manner as the first intermediate compound having a group corresponding to —$R^1$ at one terminal.

Thereafter, the second intermediate compound is reacted with an epoxy compound formed by reacting the first intermediate compound with epibromohydrin.

By performing the above-described steps, a compound which has a glycerin structure in the center of a chain structure and $R^1$ is different from $R^4$ and/or two PFPE chains represented by $R^2$ and $R^3$ are different from each other in Formula (1) can be produced.

The compound represented by Formula (1) is obtained through the above-described method.

Epoxy compounds used in producing the fluorine-containing ether compound of the present embodiment can be synthesized by reacting alcohols which have a structure corresponding to a group consisting of —$R^1$ (or —$R^4$) of the fluorine-containing ether compound to be produced with a compound having an epoxy group selected from epichlorohydrin, epibromohydrin, 2-bromoethyloxirane, and allyl glycidyl ether. Such epoxy compounds may be synthesized through a method of oxidizing an unsaturated bond, or commercially available products may be purchased and used.

Here, the function of a lubricating layer formed on a protective layer using a lubricant containing the fluorine-containing ether compound of the present embodiment will be described.

Examples of the cause of corrosion of a magnetic recording medium include ionic contamination substances present on the surface of the magnetic recording medium. Most of the ionic contamination substances adhere to the magnetic recording medium from outside during the production process of the magnetic recording medium. The ionic contamination substances may also be generated when environmental substances that have intruded into a hard disk drive (magnetic recording/reproducing device) adhere to the magnetic recording medium. Specifically, for example, water containing environmental substances such as ions may adhere to the surface of the magnetic recording medium when the magnetic recording medium and/or hard disk drive are held under high-temperature and high-humidity conditions. When water containing environmental substances such as ions passes through the lubricating layer formed on the surface of the magnetic recording medium, it condenses minute ionic components present under the lubricating layer to generate ionic contamination substances.

Since the fluorine-containing ether compound of the present embodiment is a compound represented by Formula (1), a lubricating layer containing the fluorine-containing ether compound is highly effective in suppressing corrosion of a magnetic recording medium. The effect of suppressing corrosion of a magnetic recording medium is based on the synergistic effects that the lubricating layer formed on the protective layer using the lubricant containing the fluorine-containing ether compound of the present embodiment has excellent water resistance and adhesion properties with respect to the protective layer, has appropriate hydrophobicity, and is likely to be formed on the protective layer in a uniform coating state.

More specifically, the lubricating layer formed on the protective layer adheres closely to the protective layer due to the hydroxyl group (—OH) in the glycerin structure (—OCH$_2$CH(OH)CH$_2$O—) placed in the center of the chain structure of the fluorine-containing ether compound represented by Formula (1) and two or three polar groups in each of $R^1$ and $R^4$. As a result, the lubricating layer prevents contamination substances from intruding into a magnetic recording medium and suppresses corrosion of the magnetic recording medium.

In addition, in the fluorine-containing ether compound represented by Formula (1), PFPE chains represented by $R^2$ and $R^3$ are each placed between the hydroxyl group in the glycerin structure placed in the center of the chain structure and the terminal groups represented by $R^1$ and $R^4$. For this reason, the distance between the hydroxyl group in the glycerin structure and the polar groups in the terminal groups represented by $R^1$ and $R^4$ is appropriate. As a result, the hydroxyl group in the glycerin structure is less likely to be aggregated with the polar groups in the terminal groups represented by $R^1$ and $R^4$, and adheres closely to the protective layer. As a result, the fluorine-containing ether compound represented by Formula (1) can easily wet and spread on the protective layer, and the lubricating layer containing the fluorine-containing ether compound is likely to be formed in a uniform coating state. The lubricating layer formed in a uniform coating state has a high coating rate, which makes it difficult for environmental substances that generate contamination substances to intrude through voids, so corrosion of the magnetic recording medium can be suppressed.

In addition, the fluorine-containing ether compound represented by Formula (1) has PFPE chains represented by $R^2$ and $R^3$. The PFPE chains represented by $R^2$ and $R^3$ in the lubricating layer covers the surface of the protective layer and impart water resistance to the lubricating layer due to their low surface energy. Accordingly, the lubricating layer containing the fluorine-containing ether compound represented by Formula (1) can prevent water from intruding into the magnetic recording medium because water hardly passes therethrough, and improves corrosion resistance of the magnetic recording medium.

Furthermore, in the fluorine-containing ether compound represented by Formula (1), individual polar groups in $R^1$ and $R^4$ are bound to different carbon atoms and the carbon atoms to which the polar groups are bound are bound to each other via a linking group having a carbon atom to which the polar groups are not bound. It is thought that, under high-temperature and high-humidity conditions, fluorine-containing ether compounds cause molecular motion due to heat, and water intrudes through the voids between molecules. For this reason, even if $R^1$ and $R^4$ placed at the terminals of the molecule each contain two or three polar groups, the lubricating layer containing the fluorine-containing ether compound represented by Formula (1) has appropriate hydrophobicity due to hydrophobicity of carbon atoms to which the polar groups are bound and carbon atoms contained in the linking group. As a result, the lubricating layer prevents water from intruding into the magnetic recording medium and suppresses corrosion of the magnetic recording medium.

[Lubricant for Magnetic Recording Medium]

A lubricant for a magnetic recording medium of the present embodiment contains the fluorine-containing ether compound represented by Formula (1). The lubricant of the present embodiment can be used after being mixed as necessary with a well-known material that is used as a material for lubricants within the scope not impairing the characteristics imparted by containing the fluorine-containing ether compound represented by Formula (1).

Specific examples of well-known materials include FOMBLIN (registered trademark) ZDIAC, FOMBLIN ZDEAL, and FOMBLIN AM-2001 (all manufactured by Solvay Solexis), and Moresco A20H (manufactured by Moresco Corporation). The number average molecular weight of the well-known material that is used by being mixed with the lubricant of the present embodiment is preferably 1,000 to 10,000.

In a case where the lubricant of the present embodiment contains a material other than the fluorine-containing ether compound represented by Formula (1), the content of the fluorine-containing ether compound represented by Formula (1) in the lubricant of the present embodiment is preferably 50 mass % or more and more preferably 70 mass % or more. The content of the fluorine-containing ether compound represented by Formula (1) may be 80 mass % or more or 90 mass % or more. However, the present invention is not limited to these examples.

Since the lubricant of the present embodiment contains the fluorine-containing ether compound represented by Formula (1), a lubricating layer highly effective in suppressing corrosion of a magnetic recording medium can be formed. The lubricating layer consisting of the lubricant of the present embodiment is highly effective in suppressing corrosion of a magnetic recording medium, and therefore can be made thin.

[Magnetic Recording Medium]

A magnetic recording medium of the present embodiment includes at least a magnetic layer, a protective layer, and a lubricating layer sequentially provided on a substrate.

In the magnetic recording medium of the present embodiment, one or more underlayers can be provided as necessary between the substrate and the magnetic layer. In addition, it is also possible to provide an adhesive layer and/or a soft magnetic layer between the underlayer and the substrate.

The FIGURE is a schematic cross-sectional view showing one embodiment of a magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

As the substrate 11, for example, a non-magnetic substrate or the like in which a NiP or NiP alloy film is formed on a base made of metal or alloy material such as Al or an Al alloy can be used.

In addition, as the substrate 11, a non-magnetic substrate made of a non-metal material such as glass, ceramics, silicon, silicon carbide, carbon or a resin may be used, and a non-magnetic substrate in which a NiP or NiP alloy film is formed on a base made of this non-metal material may also be used.

"Adhesive Layer"

The adhesive layer 12 prevents the progress of corrosion of the substrate 11 which may occur in a case where the substrate 11 and the soft magnetic layer 13, which is provided on the adhesive layer 12, are arranged in contact with each other. The material of the adhesive layer 12 can be appropriately selected from, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 preferably has a structure in which a first soft magnetic film, an interlayer made of a Ru film, and a second soft magnetic film are sequentially laminated. That is, the soft magnetic layer 13 preferably has a structure in which the interlayer made of a Ru film is sandwiched between the two soft magnetic films, whereby the soft magnetic films on and under the interlayer are antiferromagnetically coupled (AFC).

Examples of the material of the first soft magnetic film and the second soft magnetic film include a CoZrTa alloy and a CoFe alloy.

Any of Zr, Ta and Nb is preferably added to the CoFe alloy that is used for the first soft magnetic film and the second soft magnetic film. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer for controlling the orientations and crystal sizes of the second underlayer 15 and the magnetic layer 16 that are provided on the first underlayer 14.

Examples of the first underlayer 14 include a Cr layer, a Ta layer, a Ru layer, a CrMo alloy layer, a CoW alloy layer, a CrW alloy layer, a CrV alloy layer, and a CrTi alloy layer.

The first underlayer 14 can be formed by, for example, a sputtering method.

"Second Underlayer"

The second underlayer 15 is a layer that controls the orientation of the magnetic layer 16 to be favorable. The second underlayer 15 is preferably a Ru or Ru alloy layer. The second underlayer 15 may be a single layer or may be composed of a plurality of layers. In a case where the second underlayer 15 is composed of a plurality of layers, all of the layers may be composed of the same material or at least one layer may be composed of a different material.

The second underlayer 15 can be formed by, for example, a sputtering method.

"Magnetic Layer"

The magnetic layer 16 is made of a magnetic film in which the easy magnetization axis is directed in a perpendicular or parallel direction with respect to the substrate surface. The magnetic layer 16 is a layer containing Co and Pt and may be a layer further containing an oxide or Cr, B, Cu, Ta, Zr, or the like in order to improve SNR characteristics.

Examples of the oxide that is contained in the magnetic layer 16 include $SiO_2$, $SiO$, $Cr_2O_3$, $CoO$, $Ta_2O_3$, and $TiO_2$.

The magnetic layer 16 may be composed of a single layer or may be composed of a plurality of magnetic layers made of materials with different compositions. For example, in a case where the magnetic layer 16 is composed of three layers of a first magnetic layer, a second magnetic layer, and a third magnetic layer sequentially laminated from below, the first magnetic layer is preferably a granular structure made of a material containing Co, Cr, and Pt and further containing an oxide. As the oxide that is contained in the first magnetic layer, for example, oxides of Cr, Si, Ta, Al, Ti, Mg, Co, or the like are preferably used. Among them, in particular, $TiO_2$, $Cr_2O_3$, $SiO_2$, and the like can be suitably used. In addition, the first magnetic layer is preferably made of a composite oxide to which two or more oxides have been added. Among them, in particular, $Cr_2O_3$—$SiO_2$, $Cr_2O_3$—$TiO_2$, $SiO_2$—$TiO_2$, and the like can be suitably used.

The first magnetic layer may contain, in addition to Co, Cr, Pt, and the oxide, one or more elements selected from B, Ta, Mo, Cu, Nd, W, Nb, Sm, Tb, Ru, and Re. For the second magnetic layer, the same material as for the first magnetic layer can be used. The second magnetic layer preferably has a granular structure.

The third magnetic layer preferably has a non-granular structure made of a material containing Co, Cr, and Pt but containing no oxides. The third magnetic layer may contain, in addition to Co, Cr, and Pt, one or more elements selected from B, Ta, Mo, Cu, Nd, W, Nb, Sm, Tb, Ru, Re, and Mn.

In a case where the magnetic layer 16 is formed of a plurality of magnetic layers, a non-magnetic layer is preferably provided between the magnetic layers adjacent to each other. In a case where the magnetic layer 16 is made up of three layers of the first magnetic layer, the second magnetic layer and the third magnetic layer, it is preferable to provide a non-magnetic layer between the first magnetic layer and the second magnetic layer and a non-magnetic layer between the second magnetic layer and the third magnetic layer.

For the non-magnetic layer that is provided between the magnetic layers adjacent to each other in the magnetic layer 16, it is possible to suitably use, for example, Ru, a Ru alloy, a CoCr alloy, and a CoCrXT alloy (X1 represents one or more elements selected from Pt, Ta, Zr, Re, Ru, Cu, Nb, Ni, Mn, Ge, Si, O, N, W, Mo, Ti, V, and B).

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, $MgO$, $Y_2O_3$, and $TiO_2$ can be used. As the metallic nitride, for example, $AlN$, $Si_3N_4$, $TaN$, and $CrN$ can be used. As the metallic carbide, for example, $TaC$, $BC$, and $SiC$ can be used.

The non-magnetic layer can be formed by, for example, a sputtering method.

The magnetic layer 16 is preferably a magnetic layer for perpendicular magnetic recording in which the easy magnetization axis is directed in a direction perpendicular to the substrate surface in order to realize a higher recording density. The magnetic layer 16 may be a magnetic layer for in-plane magnetic recording.

The magnetic layer 16 may be formed by any well-known conventional method such as a deposition method, an ion beam sputtering method, or a magnetron sputtering method. The magnetic layer 16 is normally formed by a sputtering method.

"Protective layer" The protective layer 17 protects the magnetic layer 16. The protective layer 17 may be composed of a single layer or may be composed of a plurality of layers. As the material of the protective layer 17, carbon, nitrogen-containing carbon, silicon carbide, and the like can be exemplified.

As the protective layer 17, a carbon-based protective layer can be preferably used, and, in particular, an amorphous carbon protective layer is preferable. When the protective layer 17 is a carbon-based protective layer, an interaction with the hydroxyl group contained in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon-based protective layer. The carbon-based protective layer is suitably formed as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and the adhesive force between the lubricating layer 18 and the carbon-based protective layer further improve.

The film thickness of the protective layer 17 may be set to 1 nm to 7 nm. When the film thickness of the protective layer 17 is 1 nm or more, performance as the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target material is used, a chemical vapor deposition (CVD) method in which a hydrocarbon raw material such as ethylene or toluene is used, an ion beam deposition (IBD) method, and the like. In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

"Lubricating Layer"

The lubricating layer 18 prevents contamination of the magnetic recording medium 10. In addition, the lubricating layer 18 reduces frictional force of a magnetic head of a magnetic recording/reproducing device, which slides on the magnetic recording medium 10, thereby improving the durability of the magnetic recording medium 10.

The lubricating layer 18 is formed in contact with the protective layer 17 as shown in the FIGURE. The lubricating layer 18 contains the above-described fluorine-containing ether compound.

In a case where the protective layer 17, which is placed below the lubricating layer 18, is a carbon-based protective layer, particularly, the lubricating layer 18 is bound to the protective layer 17 with a high binding force. As a result, the magnetic recording medium 10 in which the surface of the protective layer 17 is coated with the lubricating layer 18 at a high coating rate in spite of a thin thickness is likely to be obtained, and contamination on the surface of the magnetic recording medium 10 can be effectively prevented.

The average film thickness of the lubricating layer 18 is preferably 0.5 nm (5 Å) to 2.0 nm (20 Å) and more preferably 0.5 nm (5 Å) to 1.0 nm (10 Å). When the average film thickness of the lubricating layer 18 is 0.5 nm or more, the lubricating layer 18 does not have an island shape or a mesh shape and is formed in a uniform film thickness. For this reason, the surface of the protective layer 17 can be coated with the lubricating layer 18 at a high coating rate. In addition, when the average film thickness of the lubricating layer 18 is set to 2.0 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes into the layer below the lubricating layer 18. The environmental substance that has intruded into the layer below the lubricating layer 18 is adsorbed and bound to the protective layer 17 and generates a contamination substance. At the time of reproducing magnetic records, the generated contamination substance (aggregated component) adheres (transfers) to a magnetic head as a smear to break the magnetic head or degrade the magnetic recording/reproducing characteristics of magnetic recording/reproducing devices.

Examples of the environmental substance that generates the contamination substance include siloxane compounds (cyclic siloxane and linear siloxane), ionic impurities, hydrocarbons having a relatively high molecular weight such as octacosane, and plasticizers such as dioctyl phthalate. Examples of metal ions contained in the ionic impurities include a sodium ion and a potassium ion. Examples of inorganic ions contained in the ionic impurities include a chlorine ion, a bromine ion, a nitrate ion, a sulfate ion, and an ammonium ion. Examples of organic ions contained in the ionic impurities include an oxalate ion and a formate ion.

"Method for Forming Lubricating Layer"

Examples of methods for forming the lubricating layer 18 include a method in which a magnetic recording medium that is not yet fully manufactured and thus includes the individual layers up to the protective layer 17 formed on the substrate 11 is prepared and a solution for forming a lubricating layer is applied onto the protective layer 17 and dried.

The solution for forming a lubricating layer can be obtained by dispersing and dissolving the above-described lubricant for a magnetic recording medium of the embodiment in a solvent as necessary and adjusting the viscosity and concentration to be suitable for application methods.

Examples of solvents used for the solution for forming a lubricating layer include fluorine-based solvents such as VERTREL (registered trademark) XF (trade name, manufactured by Dupont-Mitsui Fluorochemicals Co., Ltd.).

A method for applying the solution for forming a lubricating layer is not particularly limited, and examples thereof include a spin coating method, a spraying method, a paper coating method, and a dipping method.

In a case of using a dipping method, it is possible to use, for example, a method shown below. First, the substrate 11 on which the individual layers up to the protective layer 17 have been formed is immersed in the solution for forming a lubricating layer that has been placed in an immersion vessel of a dip coater. Next, the substrate 11 is lifted from the immersion vessel at a predetermined speed. As a result, the solution for forming a lubricating layer is applied to the surface of the protective layer 17 on the substrate 11.

The use of the dipping method makes it possible to uniformly apply the solution for forming a lubricating layer to the surface of the protective layer 17 and makes it possible to form the lubricating layer 18 on the protective layer 17 in a uniform film thickness.

In the present embodiment, a burnishing (precision polishing) step is preferably performed after the lubricating layer 18 is formed on the surface of the substrate 11. By performing the burnishing step, projection defects and particles present on the surface of the substrate 11 on which the lubricating layer 18 has been formed can be removed, and the magnetic recording medium 10 with a smooth surface can be obtained. If the surface of the magnetic recording medium 10 is smooth, the spacing loss with a magnetic head can be reduced and the signal characteristics may improve, which is preferable.

As the burnishing step, for example, a step of scanning burnishing tape on the surface of the substrate 11 on which the lubricating layer 18 has been formed can be performed. As the burnishing tape, one made of a resin film holding abrasive grains can be used. The grain size of the abrasive grains can be set to, for example, #6000 to #20000.

In the present embodiment, a heat treatment is preferably carried out on the substrate 11 on which the lubricating layer 18 has been formed. The heat treatment improves the adhesion properties between the lubricating layer 18 and the protective layer 17 and improves the adhesive force between the lubricating layer 18 and the protective layer 17.

The heat treatment temperature is preferably set to 100° C. to 180° C. When the heat treatment temperature is 100° C. or higher, an effect on improvement in the adhesion properties between the lubricating layer 18 and the protective layer 17 can be sufficiently obtained. In addition, when the heat treatment temperature is set to 180° C. or lower, it is possible to prevent thermal decomposition of the lubricating layer 18. The heat treatment time is preferably set to 10 to 120 minutes.

The magnetic recording medium 10 of the present embodiment includes at least the magnetic layer 16, the protective layer 17, and the lubricating layer 18 sequentially provided on the substrate 11. In the magnetic recording medium 10 of the present embodiment, the lubricating layer 18 containing the above-described fluorine-containing ether compound is formed in contact with the protective layer 17. This lubricating layer 18 is highly effective in suppressing corrosion of the magnetic recording medium 10. For this reason, the magnetic recording medium 10 of the present embodiment has less contamination substances present on the surface, has excellent corrosion resistance, and has favorable reliability and durability. In addition, since the magnetic recording medium 10 of the present embodiment has the lubricating layer 18 highly effective in suppressing corrosion, the thickness of the protective layer 17 and/or the lubricating layer 18 can be reduced. In addition, in the lubricating layer 18 in the magnetic recording medium 10 of the present embodiment, foreign matters (smears) are less likely to be generated, and pickup can be suppressed.

EXAMPLES

Hereinafter, the present invention will be described more specifically with reference to examples and comparative examples. The present invention is not limited to the following examples.

Example 1

A compound represented by Formula (1A) above was produced through a method shown below.

20 g of a compound represented by $HOCH_2CF_2O(CF_2CF_2O)_m(CF_2O)_nCF_2CH_2OH$ (m indicating the average degree of polymerization in the formula was 4.5 and n indicating the average degree of polymerization was 4.5) (number average molecular weight: 1,000, molecular weight distribution: 1.1), 2.4 g of a compound represented by Formula (9) below (molecular weight: 202.3, 12 mmol), and 19 mL of t-butanol were added to a 200 mL eggplant flask under a nitrogen gas atmosphere and stirred until the mixture became uniform at room temperature. 0.67 g of potassium tert-butoxide (molecular weight: 112.21, 6 mmol) was further added to this uniform solution and reacted by being stirred at 70° C. for 16 hours.

The compound represented by Formula (9) was synthesized by oxidizing a compound obtained by protecting ethylene glycol monoallyl ether using dihydropyran.

A reaction product obtained after the reaction was cooled to 25° C., moved to a separatory funnel containing 100 mL of water, and extracted three times with 100 mL of ethyl acetate. An organic layer was washed with water and dehydrated with anhydrous sodium sulfate. After the drying agent was filtered, the filtrate was concentrated, and the residue was purified by silica gel column chromatography, thereby obtaining 9.6 g of a compound represented by Formula (10) below (molecular weight: 1202.3, 8.0 mmol) as an intermediate.

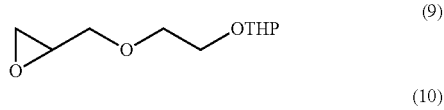

(9)

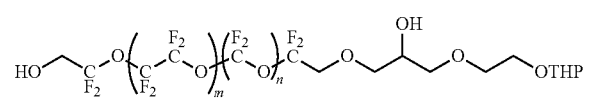

(10)

(In Formula (9), THP represents a tetrahydropyranyl group.)

(In Formula (10), m indicating the average degree of polymerization is 4.5, and n indicating the average degree of polymerization is 4.5. In Formula (10), THP represents a tetrahydropyranyl group.)

9.6 g of the compound represented by Formula (10) as an intermediate (molecular weight: 1202.3, 8.0 mmol), 5.6 mL of t-butanol, and 0.539 g of potassium tert-butoxide (molecular weight: 112.21, 4.8 mmol) were added to a 200 mL eggplant flask in a nitrogen gas atmosphere and stirred until the mixture became uniform at room temperature. 0.27 mL of epibromohydrin (molecular weight: 137, 3.3 mmol) was further added to this uniform solution and reacted by being stirred at 70° C. for 24 hours.

A reaction solution obtained after the reaction was returned to room temperature, and 31 g of a 10% hydrogen chloride/methanol solution (hydrogen chloride-methanol reagent (5% to 10%), manufactured by Tokyo Chemical Industry Co., Ltd.) was added thereto and stirred at room temperature for 2 hours. The reaction solution was moved little by little to a separatory funnel containing 100 mL of saline water and extracted three times with 200 mL of ethyl acetate. An organic layer was sequentially washed with 100 mL of saline water, 100 mL of saturated sodium bicarbonate water, and 100 mL of saline water, and dehydrated with anhydrous sodium sulfate. After the drying agent was filtered, the filtrate was concentrated, and the residue was purified by silica gel column chromatography. By performing the above-described steps, 4.1 g of a compound (1A) (in Formula (1A), ma1, ma2, na1, and na2 indicating the average degree of polymerization were 4.5) (molecular weight: 2292, 1.8 mmol) was obtained.

$^1$H-NMR measurement of the obtained compound (1A) was carried out, and the structure was identified from the following results.

$^1$H-NMR (CD$_3$COCD$_3$): δ [ppm]=3.46 to 4.24 (36H)
$^{19}$F-NMR (CD$_3$COCD$_3$): δ [ppm]=−55.6 to −50.6 (18F), −77.7 (4F), −80.3 (4F), −91.0 to −88.5 (36F)

Example 2

The same operation as in Example 1 was carried out except that 2.6 g of a compound represented by Formula (11) below was used instead of the compound represented by Formula (9), thereby obtaining 4.2 g of the compound represented by Formula (1B) above (in Formula (1B), mb1, mb2, nb1, and nb2 indicating the average degree of polymerization were 4.5).

The compound represented by Formula (11) was synthesized by protecting one hydroxyl group of 1,3-propanediol with a tetrahydropyranyl (THP) group and reacting epibromohydrin with the other hydroxyl group.

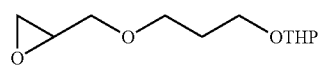

(11)

(In Formula (11), THP represents a tetrahydropyranyl group.)

$^1$H-NMR measurement of the obtained compound (1B) was carried out, and the structure was identified from the following results.

$^1$H-NMR (CD$_3$COCD$_3$): δ [ppm]=1.57 to 1.81 (411), 3.38 to 4.25 (36H)
$^{19}$F-NMR (CD$_3$COCD$_3$): δ [ppm]=−55.6 to −50.6 (18F), −77.7 (4F), −80.3 (4F), −91.0 to −88.5 (36F)

Example 3

The same operation as in Example 1 was carried out except that 2.8 g of a compound represented by Formula (12) below was used instead of the compound represented by Formula (9), thereby obtaining 4.2 g of the compound represented by Formula (1C) above (in Formula (1C), mc1, mc2, nc1, and nc2 indicating the average degree of polymerization were 4.5).

The compound represented by Formula (12) was synthesized by protecting one hydroxyl group of 1,4-butanediol with a THP group and reacting epibromohydrin with the other hydroxyl group.

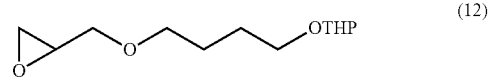

(12)

(In Formula (12), THP represents a tetrahydropyranyl group.)

$^1$H-NMR measurement of the obtained compound (1C) was carried out, and the structure was identified from the following results.

$^1$H-NMR (CD$_3$COCD$_3$): δ [ppm]=1.55 to 1.83 (8H), 3.40 to 4.25 (36H)
$^{19}$F-NMR (CD$_3$COCD$_3$): δ [ppm]=−55.6 to −50.6 (18F), −77.7 (4F), −80.3 (4F), −91.0 to −88.5 (36F)

Example 4

The same operation as in Example 1 was carried out except that 3.8 g of a compound represented by Formula (13) below was used instead of the compound represented by Formula (9), thereby obtaining 4.4 g of the compound represented by Formula (1D) above (in Formula (1D), md1, md2, nd1, and nd2 indicating the average degree of polymerization were 4.5).

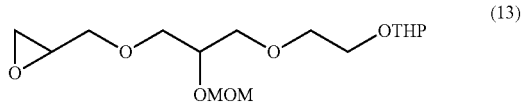

(13)

(In Formula (13), THP represents a tetrahydropyranyl group, and MOM represents a methoxymethyl group.)

The compound represented by Formula (13) was synthesized by the following method.

A tert-butyldimethylsilyl (TBS) group was introduced as a protective group into the primary hydroxyl group in 3-allyloxy-1,2-propanediol, and a methoxymethyl (MOM) group was introduced as a protective group into the secondary hydroxyl group in the obtained compound. After that, the TBS group was removed from the compound, and 2-bromoethoxytetrahydropyran was reacted with the generated primary hydroxyl group. The double bond of the obtained compound was oxidized. The compound represented by Formula (13) was obtained through the above-described steps.

$^1$H-NMR measurement of the obtained compound (1D) was carried out, and the structure was identified from the following results.

$^1$H-NMR (CD$_3$COCD$_3$): δ [ppm]=3.37 to 4.32 (48H)
$^{19}$F-NMR (CD$_3$COCD$_3$): δ [ppm]=−55.6 to −50.6 (18F), −77.7 (4F), −80.3 (4F), −91.0 to −88.5 (36F)

Example 5

The same operation as in Example 1 was carried out except that 4.0 g of a compound represented by Formula

(14) below was used instead of the compound represented by Formula (9), thereby obtaining 4.4 g of the compound represented by Formula (1E) above (in Formula (1E), me1, me2, nc1, and ne2 indicating the average degree of polymerization were 4.5).

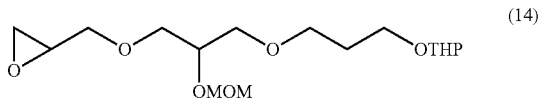

(In Formula (14), THP represents a tetrahydropyranyl group, and MOM represents a methoxymethyl group.)

The compound represented by Formula (14) was synthesized by the following method.

A TBS group was introduced into the primary hydroxyl group in 3-allyloxy-1,2-propanediol, and a MOM group was introduced into the secondary hydroxyl group in the obtained compound. After the TBS group in the obtained compound was removed, 2-(chloropropoxy)tetrahydro-2H-pyran was reacted with the generated primary hydroxyl group. The double bond of the obtained compound was oxidized. The compound represented by Formula (14) was obtained through the above-described steps.

$^1$H-NMR (CD$_3$COCD$_3$): δ [ppm]=1.50 to 1.80 (4H), 3.40 to 4.25 (48H)

$^{19}$F-NMR (CD$_3$COCD$_3$): δ [ppm]=−55.6 to −50.6 (18F), −77.7 (4F), −80.3 (4F), −91.0 to −88.5 (36F)

Example 6

The same operation as in Example 1 was carried out except that 4.2 g of a compound represented by Formula (15) below was used instead of the compound represented by Formula (9), thereby obtaining 4.5 g of the compound represented by Formula (1F) above (in Formula (1F), mf1, mf2, nf1, and nf2 indicating the average degree of polymerization were 4.5).

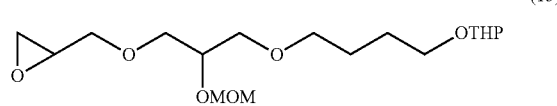

(In Formula (15), THP represents a tetrahydropyranyl group, and MOM represents a methoxymethyl group.)

The compound represented by Formula (15) was synthesized by the following method.

A TBS group was introduced into the primary hydroxyl group in 3-allyloxy-1,2-propanediol, and a MOM group was introduced into the secondary hydroxyl group in the obtained compound. After the TBS group in the obtained compound was removed, 2-(bromobutoxy)tetrahydro-2H-pyran was reacted with the generated primary hydroxyl group. The double bond of the obtained compound was oxidized. The compound represented by Formula (15) was obtained through the above-described steps.

$^1$H-NMR measurement of the obtained compound (1F) was carried out, and the structure was identified from the following results.

$^1$H-NMR (CD$_3$COCD$_3$): δ [ppm]=1.52 to 1.81 (8H), 3.44 to 4.26 (48H)

$^{19}$F-NMR (CD$_3$COCD$_3$): δ [ppm]=−55.6 to −50.6 (18F), −77.7 (4F), −80.3 (4F), −91.0 to −88.5 (36F)

Example 7

The same operation as in Example 1 was carried out except that 2.1 g of a compound represented by Formula (16) below was used instead of the compound represented by Formula (9), thereby obtaining 4.0 g of the compound represented by Formula (1G) above (in Formula (1G), mg1, mg2, ng1, and ng2 indicating the average degree of polymerization were 4.5).

The compound represented by Formula (16) was synthesized by introducing a THP group into the primary hydroxyl group in 3-buten-1-ol and oxidizing the double bond of the obtained compound.

(In Formula (16), THP represents a tetrahydropyranyl group.)

$^1$H-NMR measurement of the obtained compound (1G) was carried out, and the structure was identified from the following results.

$^1$H-NMR (CD$_3$COCD$_3$): δ [ppm]=3.50 to 4.32 (32H)

$^{19}$F-NMR (CD$_3$COCD$_3$): δ [ppm]=−55.6 to −50.6 (18F), −77.7 (4F), −80.3 (4F), −91.0 to −88.5 (36F)

Example 8

The same operation as in Example 1 was carried out except that 2.2 g of a compound represented by Formula (17) below was used instead of the compound represented by Formula (9), thereby obtaining 4.1 g of the compound represented by Formula (1H) above (in Formula (1H), mh1, mh2, nh1, and nh2 indicating the average degree of polymerization was 4.5).

The compound represented by Formula (17) was synthesized by introducing a THP group into the primary hydroxyl group in 4-penten-1-ol and oxidizing the double bond of the obtained compound.

(In Formula (17), THP represents a tetrahydropyranyl group.)

$^1$H-NMR measurement of the obtained compound (1H) was carried out, and the structure was identified from the following results.

$^1$H-NMR (CD$_3$COCD$_3$): δ [ppm]=1.38 to 1.75 (4H), 3.37 to 4.31 (32H)

$^{19}$F-NMR (CD$_3$COCD$_3$): δ [ppm]=−55.6 to −50.6 (18F), −77.7 (4F), −80.3 (4F), −91.0 to −88.5 (36F)

Example 9

The same operation as in Example 1 was carried out except that 2.6 g of a compound represented by Formula

(18) below was used instead of the compound represented by Formula (9), thereby obtaining 4.2 g of the compound represented by Formula (11) above (in Formula (11), mi1, mi2, ni1, and ni2 indicating the average degree of polymerization were 4.5).

The compound represented by Formula (18) was synthesized by introducing a THP group into the primary hydroxyl group in 6-hepten-1-ol and oxidizing the double bond of the obtained compound.

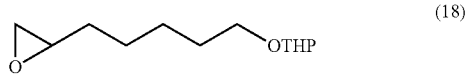

(In Formula (18), THP represents a tetrahydropyranyl group.)

$^1$H-NMR measurement of the obtained compound (1I) was carried out, and the structure was identified from the following results.

$^1$H-NMR (CD$_3$COCD$_3$): δ [ppm]=1.39 to 1.84 (12H), 3.35 to 4.35 (32H)

$^{19}$F-NMR (CD$_3$COCD$_3$): δ [ppm]=−55.6 to −50.6 (18F), −77.7 (4F), −80.3 (4F), −91.0 to −88.5 (36F)

Example 10

The same operation as in Example 1 was carried out except that 3.0 g of a compound represented by Formula (19) below was used instead of the compound represented by Formula (9), thereby obtaining 4.3 g of the compound represented by Formula (1J) above (in Formula (1J), mj1, mj2, nj1, and nj2 indicating the average degree of polymerization were 4.5).

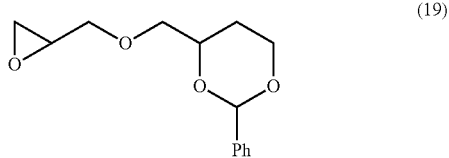 [SMILES: c1ccc(C2OCCC(COCC3CO3)O2)cc1]

(In Formula (19), Ph represents a phenyl group.)

The compound represented by Formula (19) was synthesized by the following method.

1,2,4-Butanetriol was reacted with benzaldehyde dimethylacetal to synthesize a compound in which hydroxyl groups bound to 2- and 4-position carbons of 1,2,4-butanetriol were protected. This compound was reacted with epibromohydrin to synthesize the compound represented by Formula (19).

$^1$H-NMR measurement of the obtained compound (1J) was carried out, and the structure was identified from the following results.

$^1$H-NMR (CD$_3$COCD$_3$): δ [ppm]=3.38 to 4.36 (44H)

$^{19}$F-NMR (CD$_3$COCD$_3$): δ [ppm]=−55.6 to −50.6 (18F), −77.7 (4F), −80.3 (4F), −91.0 to −88.5 (36F)

Example 11

The same operation as in Example 1 was carried out except that 2.8 g of a compound represented by Formula (20) below was used instead of the compound represented by Formula (9), thereby obtaining 4.2 g of the compound represented by Formula (1K) above (in Formula (1K), mk1, mk2, nk1, and nk2 indicating the average degree of polymerization were 4.5).

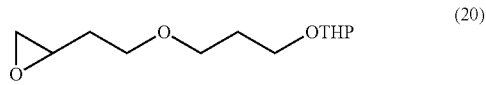

(In Formula (20), THP represents a tetrahydropyranyl group.)

The compound represented by Formula (20) was synthesized by the following method.

The compound was synthesized by oxidizing the double bond of a compound obtained by reacting 3-buten-1-ol with 2-(3-bromopropoxy)tetrahydro-2H-pyran.

$^1$H-NMR measurement of the obtained compound (1K) was carried out, and the structure was identified from the following results.

$^1$H-NMR (CD$_3$COCD$_3$): δ [ppm]=1.34 to 1.79 (4H), 3.36 to 4.32 (40H)

$^{19}$F-NMR (CD$_3$COCD$_3$): δ [ppm]=−55.6 to −50.6 (18F), −77.7 (4F), −80.3 (4F), −91.0 to −88.5 (36F)

Example 12

The same operation as in Example 1 was carried out except that 4.7 g of a compound represented by Formula (21) below was used instead of the compound represented by Formula (9), thereby obtaining 4.5 g of the compound represented by Formula (1L) above (in Formula (1L), ml1, ml2, nl1, and nl2 indicating the average degree of polymerization were 4.5).

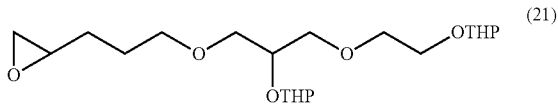

(In Formula (21), THP represents a tetrahydropyranyl group.)

The compound represented by Formula (21) was synthesized by protecting the secondary hydroxyl group of a compound obtained by reacting the compound represented by Formula (9) with the hydroxyl group of 4-penten-1-ol with a THP group and oxidizing the double bond of the obtained compound.

$^1$H-NMR measurement of the obtained compound (1L) was carried out, and the structure was identified from the following results.

$^1$H-NMR (CD$_3$COCD$_3$): δ [ppm]=1.55 to 1.78 (4H), 3.36 to 4.25 (52H)

$^{19}$F-NMR (CD$_3$COCD$_3$): δ [ppm]=−55.6 to −50.6 (18F), −77.7 (4F), −80.3 (4F), −91.0 to −88.5 (36F)

Example 13

An intermediate (molecular weight: 1186.2, 4.0 mmol) of Example 13 was obtained in the same manner as the intermediate of Example 1 except that the compound represented by Formula (17) above was used instead of the compound represented by Formula (9).

4.8 g of the compound represented by Formula (10) as an intermediate (molecular weight: 1202.3, 4.0 mmol) of Example 1, 5.6 mL of t-butanol, and 0.45 g of potassium tert-butoxide (molecular weight: 112.21, 4.0 mmol) were added to a 200 mL eggplant flask in a nitrogen gas atmosphere and stirred until the mixture became uniform at room temperature. 0.33 mL of epibromohydrin (molecular weight: 137, 4.0 mmol) was added to this uniform solution and reacted by being stirred at 70° C. for 24 hours.

4.75 g of the intermediate of Example 13 was added to the obtained reaction solution and stirred until the mixture became uniform. 0.45 g of potassium tert-butoxide (molecular weight: 112.21, 4.0 mmol) was added to this uniform solution and reacted by being stirred at 70° C. for 24 hours.

The reaction solution obtained after the reaction was returned to room temperature, and 33 g of a 10% hydrogen chloride/methanol solution (hydrogen chloride-methanol reagent (5% to 10%) manufactured by Tokyo Chemical Industry Co., Ltd.) was added thereto and stirred at room temperature for 2 hours. The reaction solution was moved little by little to a separatory funnel containing 100 mL of saline water and extracted three times with 200 mL of ethyl acetate. An organic layer was sequentially washed with 100 mL of saline water, 100 mL of saturated sodium bicarbonate water, and 100 mL of saline water, and dehydrated with anhydrous sodium sulfate. After the drying agent was filtered, the filtrate was concentrated, and the residue was purified by silica gel column chromatography. By performing the above-described steps, 4.1 g of a compound (1M) (in Formula (1M), mm, mm2, nm1, and nm2 indicating the average degree of polymerization were 4.5) (molecular weight: 2276.4, 1.8 mmol) was obtained.

$^1$H-NMR measurement of the obtained compound (1M) was carried out, and the structure was identified from the following results.

$^1$H-NMR (CD$_3$COCD$_3$): δ [ppm]=1.38 to 1.75 (2H), 3.37 to 4.31 (34H)

$^{19}$F-NMR (CD$_3$COCD$_3$): δ [ppm]=−55.6 to −50.6 (18F), −77.7 (4F), −80.3 (4F), −91.0 to −88.5 (36F)

Example 14

A compound represented by Formula (2 Å) above was produced through a method shown below.

The same operation as in Example 1 was carried out except that the compound represented by HOCH$_2$CF$_2$O(CF$_2$CF$_2$O)$_m$(CF$_2$O)$_n$CF$_2$CH$_2$OH (m' indicating the average degree of polymerization in the formula was 7.1 and n' indicating the average degree of polymerization was 0) (number average molecular weight: 1,000, molecular weight distribution: 1.1) was used instead of the compound represented by HOCH$_2$CF$_2$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5) (number average molecular weight: 1,000, molecular weight distribution: 1.1) in Example 1, thereby obtaining 4.0 g of a compound (2A) (in Formula (2 Å), m'a1 and m'a2 indicating the average degree of polymerization were 7.1).

$^1$H-NMR measurement of the obtained compound (2A) was carried out, and the structure was identified from the following results.

$^1$H-NMR (CD$_3$COCD$_3$): δ [ppm]=3.46 to 4.24 (36H)

$^{19}$F-NMR (acetone-D$_6$): δ [ppm]=−78.6 (4F), −81.3 (4F), −90.0 to −88.5 (56F)

Example 15

A compound represented by Formula (2B) above was produced through a method shown below.

The same operation as in Example 14 was carried out except that the compound represented by Formula (11) above was used instead of the compound represented by Formula (9) above, thereby obtaining 4.2 g of a compound (2B) (in Formula (2B), m'b1 and m'b2 indicating the average degree of polymerization were 7.1).

$^1$H-NMR measurement of the obtained compound (2B) was carried out, and the structure was identified from the following results.

$^1$H-NMR (CD$_3$COCD$_3$): δ [ppm]=1.57 to 1.81 (4H), 3.38 to 4.25 (36H)

$^{19}$F-NMR (acetone-D$_6$): δ [ppm]=−78.6 (4F), −81.3 (4F), −90.0 to −88.5 (56F)

Example 16

A compound represented by Formula (2C) above was produced through a method shown below.

The same operation as in Example 14 was carried out except that the compound represented by Formula (12) above was used instead of the compound represented by Formula (9) above, thereby obtaining 4.2 g of a compound (2C) (in Formula (2C), m'c1 and m'c2 indicating the average degree of polymerization were 7.1).

$^1$H-NMR measurement of the obtained compound (2C) was carried out, and the structure was identified from the following results.

$^1$H-NMR (CD$_3$COCD$_3$): δ [ppm]=1.55 to 1.83 (8H), 3.40 to 4.25 (36H)

$^{19}$F-NMR (acetone-D$_6$): δ [ppm]=−78.6 (4F), −81.3 (4F), −90.0 to −88.5 (56F)

Example 17

A compound represented by Formula (2D) above was produced through a method shown below.

The same operation as in Example 14 was carried out except that the compound represented by Formula (13) above was used instead of the compound represented by Formula (9) above, thereby obtaining 4.4 g of a compound (2D) (in Formula (2D), m'd1 and m'd2 indicating the average degree of polymerization were 7.1).

$^1$H-NMR measurement of the obtained compound (2D) was carried out, and the structure was identified from the following results.

$^1$H-NMR (CD$_3$COCD$_3$): δ [ppm]=3.37 to 4.32 (48H)

$^{19}$F-NMR (acetone-D$_6$): δ [ppm]=−78.6 (4F), −81.3 (4F), −90.0 to −88.5 (56F)

Example 18

A compound represented by Formula (2E) above was produced through a method shown below.

The same operation as in Example 14 was carried out except that the compound represented by Formula (14) above was used instead of the compound represented by Formula (9) above, thereby obtaining 4.4 g of a compound (2E) (in Formula (2E), m'e1 and m'e2 indicating the average degree of polymerization were 7.1).

$^1$H-NMR measurement of the obtained compound (2E) was carried out, and the structure was identified from the following results.

$^1$H-NMR (CD$_3$COCD$_3$): δ [ppm]=1.50 to 1.80 (4H), 3.40 to 4.25 (48H)

$^{19}$F-NMR (acetone-D$_6$): δ [ppm]=−78.6 (4F), −81.3 (4F), −90.0 to −88.5 (56F)

Example 19

A compound represented by Formula (2F) above was produced through a method shown below.

The same operation as in Example 14 was carried out except that the compound represented by Formula (15) above was used instead of the compound represented by Formula (9) above, thereby obtaining 4.5 g of a compound (2F) (in Formula (2F), m'f1 and m'f2 indicating the average degree of polymerization were 7.1).

$^1$H-NMR measurement of the obtained compound (2F) was carried out, and the structure was identified from the following results.

$^1$H-NMR (CD$_3$COCD$_3$): δ [ppm]=1.52 to 1.81 (8H), 3.44 to 4.26 (48H)

$^{19}$F-NMR (acetone-D$_6$): δ [ppm]=−78.6 (4F), −81.3 (4F), −90.0 to −88.5 (56F)

Example 20

A compound represented by Formula (2G) above was produced through a method shown below.

The same operation as in Example 14 was carried out except that the compound represented by Formula (16) above was used instead of the compound represented by Formula (9) above, thereby obtaining 4.0 g of a compound (2G) (in Formula (2G), m'g1 and m'g2 indicating the average degree of polymerization were 7.1).

$^1$H-NMR measurement of the obtained compound (2G) was carried out, and the structure was identified from the following results.

$^1$H-NMR (CD$_3$COCD$_3$): δ [ppm]=3.50 to 4.32 (32H)

$^{19}$F-NMR (acetone-D$_6$): δ [ppm]=−78.6 (4F), −81.3 (4F), −90.0 to −88.5 (56F)

Example 21

A compound represented by Formula (2H) above was produced through a method shown below.

The same operation as in Example 14 was carried out except that the compound represented by Formula (17) above was used instead of the compound represented by Formula (9) above, thereby obtaining 4.1 g of a compound (2H) (in Formula (2H), m'h1 and m'h2 indicating the average degree of polymerization were 7.1).

$^1$H-NMR measurement of the obtained compound (2H) was carried out, and the structure was identified from the following results.

$^1$H-NMR (CD$_3$COCD$_3$): δ [ppm]=1.38 to 1.75 (4H), 3.37 to 4.31 (32H)

$^{19}$F-NMR (acetone-D$_6$): a [ppm]=−78.6 (4F), −81.3 (4F), −90.0 to −88.5 (56F)

Example 22

A compound represented by Formula (2I) above was produced through a method shown below.

The same operation as in Example 14 was carried out except that the compound represented by Formula (18) above was used instead of the compound represented by Formula (9) above, thereby obtaining 4.1 g of a compound (2I) (in Formula (2I), m'i1 and m'i2 indicating the average degree of polymerization were 7.1).

$^1$H-NMR measurement of the obtained compound (2I) was carried out, and the structure was identified from the following results.

$^1$H-NMR (CD$_3$COCD$_3$): a [ppm]=1.39 to 1.84 (12H), 3.35 to 4.35 (32H)

$^{19}$F-NMR (acetone-D$_6$): δ [ppm]=−78.6 (4F), −81.3 (4F), −90.0 to −88.5 (56F)

Example 23

A compound represented by Formula (2J) above was produced through a method shown below.

The same operation as in Example 14 was carried out except that the compound represented by Formula (19) above was used instead of the compound represented by Formula (9) above, thereby obtaining 4.3 g of a compound (2J) (in Formula (2J), m'j1 and m'j2 indicating the average degree of polymerization were 7.1).

$^1$H-NMR measurement of the obtained compound (2J) was carried out, and the structure was identified from the following results.

$^1$H-NMR (CD$_3$COCD$_3$): δ [ppm]=3.38 to 4.36 (44H)

$^{19}$F-NMR (acetone-D$_6$): δ [ppm]=−78.6 (4F), −81.3 (4F), −90.0 to −88.5 (56F)

Example 24

A compound represented by Formula (2K) above was produced through a method shown below.

The same operation as in Example 14 was carried out except that the compound represented by Formula (20) above was used instead of the compound represented by Formula (9) above, thereby obtaining 4.2 g of a compound (2K) (in Formula (2K), m'k1 and m'k2 indicating the average degree of polymerization were 7.1).

$^1$H-NMR measurement of the obtained compound (2K) was carried out, and the structure was identified from the following results.

$^1$H-NMR (CD$_3$COCD$_3$): δ [ppm]=1.34 to 1.79 (4H), 3.36 to 4.32 (40H)

$^{19}$F-NMR (acetone-D$_6$): δ [ppm]=−78.6 (4F), −81.3 (4F), −90.0 to −88.5 (56F)

Example 25

A compound represented by Formula (2L) above was produced through a method shown below.

The same operation as in Example 14 was carried out except that the compound represented by Formula (21) above was used instead of the compound represented by Formula (9) above, thereby obtaining 4.1 g of a compound (2L) (in Formula (2L), m'l1 and m'l2 indicating the average degree of polymerization were 7.1).

$^1$H-NMR measurement of the obtained compound (2L) was carried out, and the structure was identified from the following results.

$^1$H-NMR (CD$_3$COCD$_3$): δ [ppm]=1.55 to 1.78 (4H), 3.36 to 4.25 (52H)

$^{19}$F-NMR (acetone-D$_6$): δ [ppm]=−78.6 (4F), −81.3 (4F), −90.0 to −88.5 (56F)

Example 26

A compound represented by Formula (3 Å) above was produced through a method shown below.

The same operation as in Example 1 was carried out except that the compound represented by $HOCH_2CF_2CF_2O(CF_2CF_2CF_2O)_pCF_2CF_2CH_2OH$ (p indicating the average degree of polymerization in the formula was 4.4) (number average molecular weight: 1,000, molecular weight distribution: 1.1) was used instead of the compound represented by $HOCH_2CF_2O(CF_2CF_2O)_m(CF_2O)_nCF_2CH_2OH$ (m indicating the average degree of polymerization in the formula was 4.5 and n indicating the average degree of polymerization was 4.5) (number average molecular weight: 1,000, molecular weight distribution: 1.1) in Example 1, thereby obtaining 4.0 g of a compound (3A) (in Formula (3A), pa1 and pa2 indicating the average degree of polymerization were 4.4).

$^1$H-NMR measurement of the obtained compound (3A) was carried out, and the structure was identified from the following results.

$^1$H-NMR ($CD_3COCD_3$): δ [ppm]=3.46 to 4.24 (36H)
$^{19}$F-NMR (acetone-$D_6$): δ [ppm]=−84.0 to −83.0 (35F), −86.4 (8F), −124.3 (8F), −130.0 to −129.0 (17F)

Example 27

A compound represented by Formula (3B) above was produced through a method shown below.

The same operation as in Example 26 was carried out except that the compound represented by Formula (11) above was used instead of the compound represented by Formula (9) above, thereby obtaining 4.2 g of a compound (3B) (in Formula (3B), pb1 and pb2 indicating the average degree of polymerization were 4.4).

$^1$H-NMR measurement of the obtained compound (3B) was carried out, and the structure was identified from the following results.

$^1$H-NMR ($CD_3COCD_3$): δ [ppm]=1.57 to 1.81 (4H), 3.38 to 4.25 (36H)
$^{19}$F-NMR (acetone-$D_6$): δ [ppm]=−84.0 to −83.0 (35F), −86.4 (8F), −124.3 (8F), −130.0 to −129.0 (17F)

Example 28

A compound represented by Formula (3C) above was produced through a method shown below.

The same operation as in Example 26 was carried out except that the compound represented by Formula (12) above was used instead of the compound represented by Formula (9) above, thereby obtaining 4.2 g of a compound (3C) (in Formula (3C), pc1 and pc2 indicating the average degree of polymerization were 4.4).

$^1$H-NMR measurement of the obtained compound (3C) was carried out, and the structure was identified from the following results.

$^1$H-NMR ($CD_3COCD_3$): δ [ppm]=1.55 to 1.83 (8H), 3.40 to 4.25 (36H)
$^{19}$F-NMR (acetone-$D_6$): δ [ppm]=−84.0 to −83.0 (35F), −86.4 (8F), −124.3 (8F), −130.0 to −129.0 (17F)

Example 29

A compound represented by Formula (3D) above was produced through a method shown below.

The same operation as in Example 26 was carried out except that the compound represented by Formula (13) above was used instead of the compound represented by Formula (9) above, thereby obtaining 4.4 g of a compound (3D) (in Formula (3D), pd1 and pd2 indicating the average degree of polymerization were 4.4).

$^1$H-NMR measurement of the obtained compound (3D) was carried out, and the structure was identified from the following results.

$^1$H-NMR ($CD_3COCD_3$): δ [ppm]=3.37 to 4.32 (48H)
$^{19}$F-NMR (acetone-$D_6$): δ [ppm]=−84.0 to −83.0 (35F), −86.4 (8F), −124.3 (8F), −130.0 to −129.0 (17F)

Example 30

A compound represented by Formula (3E) above was produced through a method shown below.

The same operation as in Example 26 was carried out except that the compound represented by Formula (14) above was used instead of the compound represented by Formula (9) above, thereby obtaining 4.4 g of a compound (3E) (in Formula (3E), pe1 and pe2 indicating the average degree of polymerization were 4.4).

$^1$H-NMR measurement of the obtained compound (3E) was carried out, and the structure was identified from the following results.

$^1$H-NMR ($CD_3COCD_3$): δ [ppm]=1.50 to 1.80 (4H), 3.40 to 4.25 (48H)
$^{19}$F-NMR (acetone-$D_6$): δ [ppm]=−84.0 to −83.0 (35F), −86.4 (8F), −124.3 (8F), −130.0 to −129.0 (17F)

Example 31

A compound represented by Formula (3F) above was produced through a method shown below.

The same operation as in Example 26 was carried out except that the compound represented by Formula (15) above was used instead of the compound represented by Formula (9) above, thereby obtaining 4.5 g of a compound (3F) (in Formula (3F), pf1 and pf2 indicating the average degree of polymerization were 4.4).

$^1$H-NMR measurement of the obtained compound (3F) was carried out, and the structure was identified from the following results.

$^1$H-NMR ($CD_3COCD_3$): δ [ppm]=1.52 to 1.81 (8H), 3.44 to 4.26 (48H)
$^{19}$F-NMR (acetone-$D_6$): δ [ppm]=−84.0 to −83.0 (35F), −86.4 (8F), −124.3 (8F), −130.0 to −129.0 (17F)

Example 32

A compound represented by Formula (3G) above was produced through a method shown below.

The same operation as in Example 26 was carried out except that the compound represented by Formula (16) above was used instead of the compound represented by Formula (9) above, thereby obtaining 4.0 g of a compound (3G) (in Formula (3G), pg1 and pg2 indicating the average degree of polymerization were 4.4).

$^1$H-NMR measurement of the obtained compound (3G) was carried out, and the structure was identified from the following results.

$^1$H-NMR (CD$_3$COCD$_3$): δ [ppm]=3.50 to 4.32 (32H)
$^{19}$F-NMR (acetone-D$_6$): δ [ppm]=−84.0 to −83.0 (35F), −86.4 (8F), −124.3 (8F), −130.0 to −129.0 (17F)

Example 33

A compound represented by Formula (3H) above was produced through a method shown below.

The same operation as in Example 26 was carried out except that the compound represented by Formula (17) above was used instead of the compound represented by Formula (9) above, thereby obtaining 4.1 g of a compound (3H) (in Formula (3H), ph1 and ph2 indicating the average degree of polymerization were 4.4).

$^1$H-NMR measurement of the obtained compound (3H) was carried out, and the structure was identified from the following results.

$^1$H-NMR (CD$_3$COCD$_3$): δ [ppm]=1.38 to 1.75 (4H), 3.37 to 4.31 (32H)
$^{19}$F-NMR (acetone-D$_6$): δ [ppm]=−84.0 to −83.0 (35F), −86.4 (8F), −124.3 (8F), −130.0 to −129.0 (17F)

Example 34

A compound represented by Formula (3I) above was produced through a method shown below.

The same operation as in Example 26 was carried out except that the compound represented by Formula (18) above was used instead of the compound represented by Formula (9) above, thereby obtaining 4.1 g of a compound (3I) (in Formula (3I), pi1 and pi2 indicating the average degree of polymerization were 4.4).

$^1$H-NMR measurement of the obtained compound (3I) was carried out, and the structure was identified from the following results.

$^1$H-NMR (CD$_3$COCD$_3$): δ [ppm]=1.39 to 1.84 (12H), 3.35 to 4.35 (32H)
$^{19}$F-NMR (acetone-D$_6$): δ [ppm]=−84.0 to −83.0 (35F), −86.4 (8F), −124.3 (8F), −130.0 to −129.0 (17F)

Example 35

A compound represented by Formula (3J) above was produced through a method shown below.

The same operation as in Example 26 was carried out except that the compound represented by Formula (19) above was used instead of the compound represented by Formula (9) above, thereby obtaining 4.3 g of a compound (3J) (in Formula (3J), pj1 and pj2 indicating the average degree of polymerization were 4.4).

$^1$H-NMR measurement of the obtained compound (3J) was carried out, and the structure was identified from the following results.

$^1$H-NMR (CD$_3$COCD$_3$): δ [ppm]=3.38 to 4.36 (44H)
$^{19}$F-NMR (acetone-D$_6$): δ [ppm]=−84.0 to −83.0 (35F), −86.4 (8F), −124.3 (8F), −130.0 to −129.0 (17F)

Example 361

A compound represented by Formula (3K) above was produced through a method shown below.

The same operation as in Example 26 was carried out except that the compound represented by Formula (20) above was used instead of the compound represented by Formula (9) above, thereby obtaining 4.2 g of a compound (3K) (in Formula (3K), pk1 and pk2 indicating the average degree of polymerization were 4.4).

$^1$H-NMR measurement of the obtained compound (3K) was carried out, and the structure was identified from the following results.

$^1$H-NMR (CD$_3$COCD$_3$): δ [ppm]=1.34 to 1.79 (4H), 3.36 to 4.32 (40H)
$^{19}$F-NMR (acetone-D$_6$): δ [ppm]=−84.0 to −83.0 (35F), −86.4 (8F), −124.3 (8F), −130.0 to −129.0 (17F)

Example 37

A compound represented by Formula (3L) above was produced through a method shown below.

The same operation as in Example 26 was carried out except that the compound represented by Formula (21) above was used instead of the compound represented by Formula (9) above, thereby obtaining 4.2 g of a compound (3L) (in Formula (3L), pl1 and pl2 indicating the average degree of polymerization were 4.4).

$^1$H-NMR measurement of the obtained compound (3L) was carried out, and the structure was identified from the following results.

$^1$H-NMR (CD$_3$COCD$_3$): δ [ppm]=1.55 to 1.78 (4H), 3.36 to 4.25 (52H)
$^{19}$F-NMR (acetone-D$_6$): δ [ppm]=−84.0 to −83.0 (35F), −86.4 (8F), −124.3 (8F), −130.0 to −129.0 (17F)

Example 38

A compound represented by Formula (4 Å) above was produced through a method shown below.

The same operation as in Example 1 was carried out except that the compound represented by HOCH$_2$CF$_2$CF$_2$CF$_2$O(CF$_2$CF$_2$CF$_2$CF$_2$O)$_q$CF$_2$CF$_2$CF$_2$CH$_2$OH (q indicating the average degree of polymerization in the formula was 3.0) (number average molecular weight: 1,000, molecular weight distribution: 1.1) was used instead of the compound represented by HOCH$_2$CF$_2$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5) (number average molecular weight: 1,000, molecular weight distribution: 1.1) in Example 1, thereby obtaining 4.3 g of a compound (4A) (in Formula (4 Å), qa1 and qa2 indicating the average degree of polymerization were 3.0).

$^1$H-NMR measurement of the obtained compound (4A) was carried out, and the structure was identified from the following results.

$^1$H-NMR (CD$_3$COCD$_3$): δ [ppm]=3.46 to 4.24 (36H)
$^{19}$F-NMR (acetone-D$_6$): δ [ppm]=−84.0 to −83.0 (32F), −122.5 (8F), −126.0 (24F), −129.0 to −128.0 (8F)

Comparative Example 11

A compound represented by Formula (1X) below was synthesized by the method described in Patent Document 2.

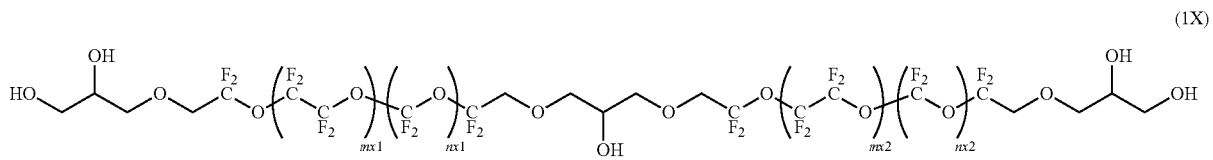

(1X)

(In Formula (1X), mx1, mx2, nx1, and nx2 indicating the average degree of polymerization were 4.5.)

$^1$H-NMR measurement of the obtained compound (1X) was carried out, and the structure was identified from the following results.

$^1$H-NMR (CD$_3$COCD$_3$): δ [ppm]=3.42 to 4.29 (28H)
$^{19}$F-NMR (CD$_3$COCD$_3$): δ [ppm]=−55.6 to −50.6 (18F), −77.7 (4F), −80.3 (4F), −91.0 to −88.5 (36F)

Comparative Example 2

A compound represented by Formula (2X) below was synthesized by the method described in Patent Document 2.

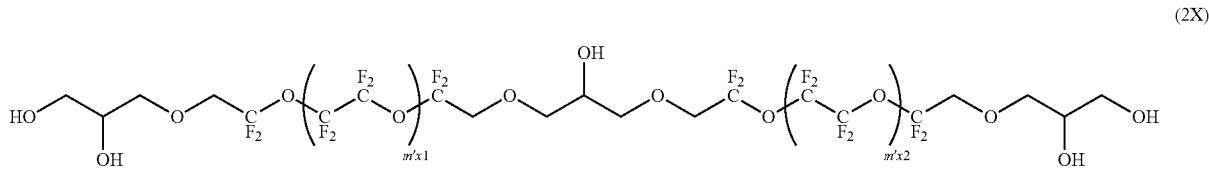

(2X)

(In Formula (2X), m'x1 and m'x2 indicating the average degree of polymerization were 7.1.)

$^1$H-NMR measurement of the obtained compound (2X) was carried out, and the structure was identified from the following results.

$^1$H-NMR (CD$_3$COCD$_3$): δ [ppm]=3.41 to 4.30 (28H)
$^{19}$F-NMR (acetone-D$_6$): a [ppm]=−78.6 (4F), −81.3 (4F), −90.0 to −88.5 (56F)

Comparative Example 3

A compound represented by Formula (3X) below was synthesized by the method described in Patent Document 2.

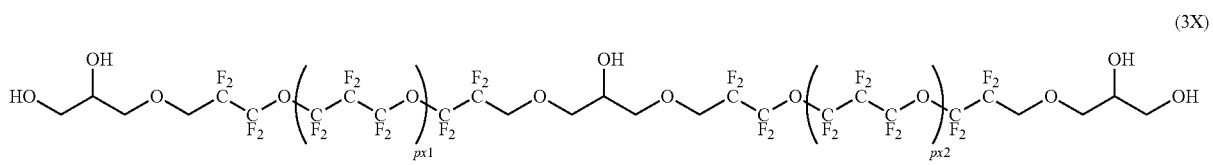

(3X)

(In Formula (3X), px1 and px2 indicating the average degree of polymerization were 4.4.)

$^1$H-NMR measurement of the obtained compound (3X) was carried out, and the structure was identified from the following results.

$^1$H-NMR (CD$_3$COCD$_3$): δ [ppm]=3.40 to 4.32 (28H)
$^{19}$F-NMR (acetone-D$_6$): δ [ppm]=−84.0 to −83.0 (35F), −86.4 (8F), −124.3 (8F), −130.0 to −129.0 (17F)

Comparative Example 41

The compound represented by Formula (1Y) below was synthesized by the following method.

The same operation as in Example 1 was carried out except that 3.8 g of a compound represented by Formula (22) below was used instead of the compound represented by Formula (9), thereby obtaining 4.2 g of the compound represented by Formula (1Y) above (in Formula (1Y), my1, my2, ny1, and ny2 indicating the average degree of polymerization were 4.5).

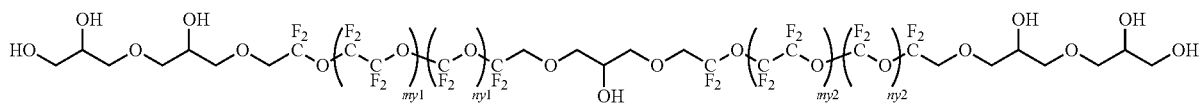

(1Y)

(In Formula (1Y), my1, my2, ny1, and ny2 indicating the average degree of polymerization were 4.5.)

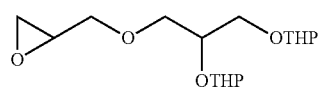

(22)

(In Formula (22), THP represents a tetrahydropyranyl group.)

The compound represented by Formula (22) was synthesized by the following method.

A THP group was introduced as a protective group to the primary and secondary hydroxyl groups of 3-allyloxy-1,2-propanediol, and the double bond of the obtained compound was oxidized. The compound represented by Formula (22) was obtained through the above-described steps.

$^1$H-NMR measurement of the obtained compound (1Y) was carried out, and the structure was identified from the following results.

$^1$H-NMR (CD$_3$COCD$_3$): δ [ppm]=3.32 to 4.23 (40H)
$^{19}$F-NMR (CD$_3$COCD$_3$): δ [ppm]=−55.6 to −50.6 (18F), −77.7 (4F), −80.3 (4F), −91.0 to −88.5 (36F)

Comparative Example 5

The compound represented by Formula (2Y) below was synthesized by the following method.

The same operation as in Example 14 was carried out except that the compound represented by Formula (22) above was used instead of the compound represented by Formula (9) above, thereby obtaining 4.2 g of a compound (2Y) (in Formula (2Y), m'y1 and m'y2 indicating the average degree of polymerization were 7.1).

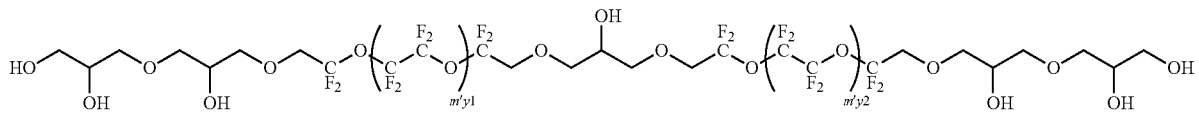

(2Y)

(In Formula (2Y), m'y1 and m'y2 indicating the average degree of polymerization were 7.1.)

$^1$H-NMR measurement of the obtained compound (2Y) was carried out, and the structure was identified from the following results.

$^1$H-NMR (CD$_3$COCD$_3$): δ [ppm]=3.32 to 4.22 (40H)

$^{19}$F-NMR (acetone-D$_6$): δ [ppm]=−78.6 (4F) to −81.3 (4F), −90.0 to −88.5 (56F)

Comparative Example 61

A compound represented by Formula (3Y) below was produced through a method shown below.

The same operation as in Example 26 was carried out except that the compound represented by Formula (22) above was used instead of the compound represented by Formula (9) above, thereby obtaining 4.2 g of a compound (3Y) (in Formula (3Y), py1 and py2 indicating the average degree of polymerization were 4.4).

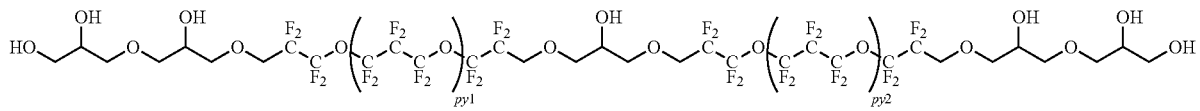

(3Y)

(In Formula (3Y), py1 and py2 indicating the average degree of polymerization were 4.4.)

$^1$H-NMR measurement of the obtained compound (3Y) was carried out, and the structure was identified from the following results.

$^1$H-NMR (CD$_3$COCD$_3$): δ [ppm]=3.30 to 4.22 (40H)

$^{19}$F-NMR (acetone-D$_6$): δ [ppm]=−84.0 to −83.0 (35F), −86.4 (8F), −124.3 (8F), −130.0 to −129.0 (17F)

Comparative Example 71

A compound represented by Formula (1Z) below was synthesized by the method described in Patent Document 4.

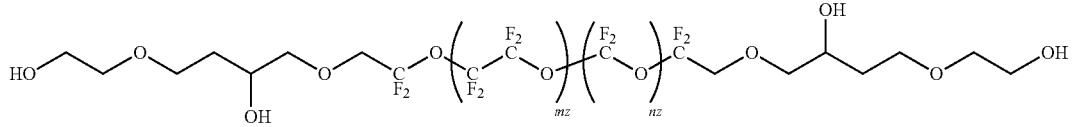

(1Z)

(In Formula (1Z), mz1 and nz2 indicating the average degree of polymerization were 4.5.)

$^1$H-NMR measurement of the obtained compound (1Z) was carried out, and the structure was identified from the following results.

$^1$H-NMR (CD$_3$COCD$_3$): δ [ppm]=1.60 to 1.79 (4H), 3.61 to 4.23 (22H)

$^{19}$F-NMR (CD$_3$COCD$_3$): δ [ppm]=−55.6 to −50.6 (9F), −77.7 (2F), −80.3 (2F), −91.0 to −88.5 (18F)

The structures of R$^1$ and R$^4$ (a, b, X, Y, and Z in Formulae (2) to (5)) and the structures of R$^2$ and R$^3$ when the compounds of Examples 1 to 38 and Comparative Examples 1 to 7 thus obtained are adapted to Formula (1) are shown in Tables 1 to 7. Regarding Comparative Example 7, the structure of both terminal groups are shown in the column for R$^1$, and the PFPE chain is shown in the column of R$^2$.

TABLE 1

| | R¹ | Formula (3) X | Formula (4) Y | Formula (4) a | Formula (2) Z | Formula (5) b | R² | R³ | R⁴ | Number average molecular weight (Mn) | Compound |
|---|---|---|---|---|---|---|---|---|---|---|---|
| Example 1 | CH₃O-CH₂-CH(OH)-CH₂-O-CH₂CH₂-OH | 1 | 0 | — | Formula (5) | 2 | Formula (6) c = 4.5 d = 4.5 | Same as R² | Same as R¹ | 2292 | (1A) |
| Example 2 | CH₃O-CH₂-CH(OH)-CH₂-O-CH₂CH₂CH₂-OH | 1 | 0 | — | Formula (5) | 3 | Formula (6) c = 4.5 d = 4.5 | Same as R² | Same as R¹ | 2320 | (1B) |
| Example 3 | CH₃O-CH₂-CH(OH)-CH₂-O-(CH₂)₄-OH | 1 | 0 | — | Formula (5) | 4 | Formula (6) c = 4.5 d = 4.5 | Same as R² | Same as R¹ | 2348 | (1C) |
| Example 4 | CH₃O-CH₂-CH(OH)-CH₂-O-CH₂-CH(OH)-CH₂-O-CH₂CH₂-OH | 2 | 0 | — | Formula (5) | 2 | Formula (6) c = 4.5 d = 4.5 | Same as R² | Same as R¹ | 2441 | (1D) |
| Example 5 | CH₃O-CH₂-CH(OH)-CH₂-O-CH₂-CH(OH)-CH₂-O-CH₂CH₂CH₂-OH | 2 | 0 | — | Formula (5) | 3 | Formula (6) c = 4.5 d = 4.5 | Same as R² | Same as R¹ | 2469 | (1E) |
| Example 6 | CH₃O-CH₂-CH(OH)-CH₂-O-CH₂-CH(OH)-CH₂-O-(CH₂)₄-OH | 2 | 0 | — | Formula (5) | 4 | Formula (6) c = 4.5 d = 4.5 | Same as R² | Same as R¹ | 2497 | (1F) |

TABLE 2

| | R¹ | Formula (3) X | Formula (4) Y | Formula (4) a | Formula (2) Z | Formula (5) b | R² | R³ | R⁴ | Number average molecular weight (Mn) | Compound |
|---|---|---|---|---|---|---|---|---|---|---|---|
| Example 7 | CH₃O-CH₂-CH(OH)-CH₂-OH | 0 | 1 | 1 | H | — | Formula (6) c = 4.5 d = 4.5 | Same as R² | Same as R¹ | 2232 | (1G) |
| Example 8 | CH₃O-CH₂-CH(OH)-CH₂-CH₂-OH | 0 | 1 | 2 | H | — | Formula (6) c = 4.5 d = 4.5 | Same as R² | Same as R¹ | 2260 | (1H) |
| Example 9 | CH₃O-CH₂-CH(OH)-(CH₂)₄-OH | 0 | 1 | 4 | H | — | Formula (6) c = 4.5 d = 4.5 | Same as R² | Same as R¹ | 2316 | (1I) |
| Example 10 | CH₃O-CH₂-CH(OH)-CH₂-O-CH₂-CH(OH)-CH₂-OH | 1 | 1 | 1 | H | — | Formula (6) c = 4.5 d = 4.5 | Same as R² | Same as R¹ | 2380 | (1J) |
| Example 11 | CH₃O-CH₂-CH(OH)-CH₂-O-CH₂CH₂CH₂-OH | 0 | 1 | 1 | Formula (5) | 3 | Formula (6) c = 4.5 d = 4.5 | Same as R² | Same as R¹ | 2348 | (1K) |
| Example 12 | CH₃O-CH₂-CH(OH)-CH₂-CH₂-O-CH₂-CH(OH)-CH₂-O-CH₂CH₂-OH | 1 | 1 | 2 | Formula (5) | 2 | Formula (6) c = 4.5 d = 4.5 | Same as R² | Same as R¹ | 2497 | (1L) |

TABLE 2-continued

| | R¹ | Formula (3) X | Formula (4) Y | a | Formula (2) Z | Formula (5) b | R² | R³ | R⁴ | Number average molecular weight (Mn) | Compound |
|---|---|---|---|---|---|---|---|---|---|---|---|
| Example 13 | (structure: ~O-CH2-CH(OH)-CH2-O-CH2CH2-OH) | 1 | 0 | — | Formula (5) | 2 | Formula (6) $c = 4.5$ $d = 4.5$ | Same as R² | Same as R¹ of Example 8 | 2276 | (1M) |

TABLE 3

| | R¹ | Formula (3) X | Formula (4) Y | a | Formula (2) Z | Formula (5) b | R² | R³ | R⁴ | Number average molecular weight (Mn) | Compound |
|---|---|---|---|---|---|---|---|---|---|---|---|
| Example 14 | (structure with OH, OH groups) | 1 | 0 | — | Formula (5) | 2 | Formula (6) $c = 7.1$ $d = 0$ | Same as R² | Same as R¹ | 2292 | (2A) |
| Example 15 | (structure) | 1 | 0 | — | Formula (5) | 3 | Formula (6) $c = 7.1$ $d = 0$ | Same as R² | Same as R¹ | 2320 | (2B) |
| Example 16 | (structure) | 1 | 0 | — | Formula (5) | 4 | Formula (6) $c = 7.1$ $d = 0$ | Same as R² | Same as R¹ | 2348 | (2C) |
| Example 17 | (structure) | 2 | 0 | — | Formula (5) | 2 | Formula (6) $c = 7.1$ $d = 0$ | Same as R² | Same as R¹ | 2441 | (2D) |
| Example 18 | (structure) | 2 | 0 | — | Formula (5) | 3 | Formula (6) $c = 7.1$ $d = 0$ | Same as R² | Same as R¹ | 2469 | (2E) |
| Example 19 | (structure) | 2 | 0 | — | Formula (5) | 4 | Formula (6) $c = 7.1$ $d = 0$ | Same as R² | Same as R¹ | 2497 | (2F) |

TABLE 4

| | R¹ | Formula (3) X | Formula (4) Y | a | Formula (2) Z | Formula (5) b | R² | R³ | R⁴ | Number average molecular weight (Mn) | Compound |
|---|---|---|---|---|---|---|---|---|---|---|---|
| Example 20 | (structure) | 0 | 1 | 1 | H | — | Formula (6) $c = 7.1$ $d = 0$ | Same as R² | Same as R¹ | 2232 | (2G) |
| Example 21 | (structure) | 0 | 1 | 2 | H | — | Formula (6) $c = 7.1$ $d = 0$ | Same as R² | Same as R¹ | 2260 | (2H) |

TABLE 4-continued

| | R$^1$ | Formula (3) X | Formula (4) Y | Formula (4) a | Formula (2) Z | Formula (5) b | R$^2$ | R$^3$ | R$^4$ | Number average molecular weight (Mn) | Compound |
|---|---|---|---|---|---|---|---|---|---|---|---|
| Example 22 | CH$_3$-O-CH$_2$-CH(OH)-CH$_2$-CH$_2$-CH$_2$-CH$_2$-OH | 0 | 1 | 4 | H | — | Formula (6) c = 7.1 d = 0 | Same as R$^2$ | Same as R$^1$ | 2316 | (2I) |
| Example 23 | CH$_3$-O-CH$_2$-CH(OH)-CH$_2$-O-CH$_2$-CH(OH)-CH$_2$-OH | 1 | 1 | 1 | H | — | Formula (6) c = 7.1 d = 0 | Same as R$^2$ | Same as R$^1$ | 2380 | (2J) |
| Example 24 | CH$_3$-O-CH$_2$-CH(OH)-CH$_2$-CH$_2$-O-CH$_2$-CH$_2$-CH$_2$-OH | 0 | 1 | 1 | Formula (5) | 3 | Formula (6) c = 7.1 d = 0 | Same as R$^2$ | Same as R$^1$ | 2348 | (2K) |
| Example 25 | CH$_3$-O-CH$_2$-CH(OH)-CH$_2$-CH$_2$-O-CH$_2$-CH(OH)-CH$_2$-O-CH$_2$-CH$_2$-OH | 1 | 1 | 2 | Formula (5) | 2 | Formula (6) c = 7.1 d = 0 | Same as R$^2$ | Same as R$^1$ | 2497 | (2L) |

TABLE 5

| | R$^1$ | Formula (3) X | Formula (4) Y | Formula (4) a | Formula (2) Z | Formula (5) b | R$^2$ | R$^3$ | R$^4$ | Number average molecular weight (Mn) | Compound |
|---|---|---|---|---|---|---|---|---|---|---|---|
| Example 26 | CH$_3$-O-CH$_2$-CH(OH)-CH$_2$-O-CH$_2$-CH$_2$-OH | 1 | 0 | — | Formula (5) | 2 | Formula (7) e = 4.4 | Same as R$^2$ | Same as R$^1$ | 2292 | (3A) |
| Example 27 | CH$_3$-O-CH$_2$-CH(OH)-CH$_2$-O-CH$_2$-CH$_2$-CH$_2$-OH | 1 | 0 | — | Formula (5) | 3 | Formula (7) e = 4.4 | Same as R$^2$ | Same as R$^1$ | 2320 | (3B) |
| Example 28 | CH$_3$-O-CH$_2$-CH(OH)-CH$_2$-O-CH$_2$-CH$_2$-CH$_2$-CH$_2$-OH | 1 | 0 | — | Formula (5) | 4 | Formula (7) e = 4.4 | Same as R$^2$ | Same as R$^1$ | 2348 | (3C) |
| Example 29 | CH$_3$-O-CH$_2$-CH(OH)-CH$_2$-O-CH$_2$-CH(OH)-CH$_2$-O-CH$_2$-CH$_2$-OH | 2 | 0 | — | Formula (5) | 2 | Formula (7) e = 4.4 | Same as R$^2$ | Same as R$^1$ | 2441 | (3D) |
| Example 30 | CH$_3$-O-CH$_2$-CH(OH)-CH$_2$-O-CH$_2$-CH(OH)-CH$_2$-O-CH$_2$-CH$_2$-CH$_2$-OH | 2 | 0 | — | Formula (5) | 3 | Formula (7) e = 4.4 | Same as R$^2$ | Same as R$^1$ | 2469 | (3E) |
| Example 31 | CH$_3$-O-CH$_2$-CH(OH)-CH$_2$-O-CH$_2$-CH(OH)-CH$_2$-O-CH$_2$-CH$_2$-CH$_2$-CH$_2$-OH | 2 | 0 | — | Formula (5) | 4 | Formula (7) e = 4.4 | Same as R$^2$ | Same as R$^1$ | 2497 | (3F) |

TABLE 6

| | R$^1$ | Formula (3) X | Formula (4) Y | Formula (4) a | Formula (2) Z | Formula (5) b | R$^2$ | R$^3$ | R$^4$ | Number average molecular weight (Mn) | Compound |
|---|---|---|---|---|---|---|---|---|---|---|---|
| Example 32 | CH$_3$-O-CH$_2$-CH(OH)-CH$_2$-OH | 0 | 1 | 1 | H | — | Formula (7) e = 4.4 | Same as R$^2$ | Same as R$^1$ | 2232 | (3G) |

TABLE 6-continued

| | R¹ | Formula (3) X | Formula (4) Y | Formula (4) a | Formula (2) Z | Formula (5) b | R² | R³ | R⁴ | Number average molecular weight (Mn) | Compound |
|---|---|---|---|---|---|---|---|---|---|---|---|
| Example 33 | 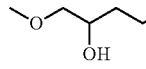 | 0 | 1 | 2 | H | — | Formula (7) e = 4.4 | Same as R² | Same as R¹ | 2260 | (3H) |
| Example 34 | 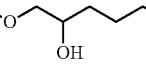 | 0 | 1 | 4 | H | — | Formula (7) e = 4.4 | Same as R² | Same as R¹ | 2316 | (3I) |
| Example 35 | 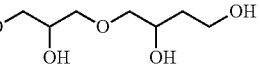 | 1 | 1 | 1 | H | — | Formula (7) e = 4.4 | Same as R² | Same as R¹ | 2380 | (3J) |
| Example 36 | 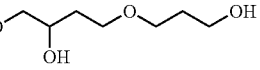 | 0 | 1 | 1 | Formula (5) | 3 | Formula (7) e = 4.4 | Same as R² | Same as R¹ | 2348 | (3K) |
| Example 37 | 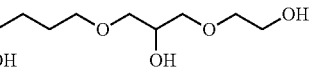 | 1 | 1 | 2 | Formula (5) | 2 | Formula (7) e = 4.4 | Same as R² | Same as R¹ | 2497 | (3L) |
| Example 38 | 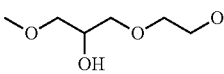 | 1 | 0 | — | Formula (5) | 2 | Formula (8) f = 3.0 | Same as R² | Same as R¹ | 2292 | (4A) |

TABLE 7

| | R¹ | R² | R³ | R⁴ | Number average molecular weight (Mn) | Compound |
|---|---|---|---|---|---|---|
| Comparative Example 1 | 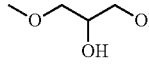 | Formula (6) c = 4.5 d = 4.5 | Same as R² | Same as R¹ | 2204 | (1X) |
| Comparative Example 2 | 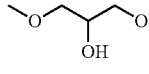 | Formula (6) c = 7.1 d = 0 | Same as R² | Same as R¹ | 2204 | (2X) |
| Comparative Example 3 | 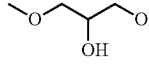 | Formula (7) e = 4.4 | Same as R² | Same as R¹ | 2204 | (3X) |
| Comparative Example 4 | 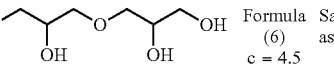 | Formula (6) c = 4.5 d = 4.5 | Same as R² | Same as R¹ | 2352 | (1Y) |
| Comparative Example 5 | 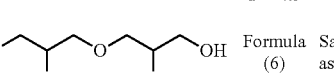 | Formula (6) c = 7.1 d = 0 | Same as R² | Same as R¹ | 2352 | (2Y) |
| Comparative Example 6 | 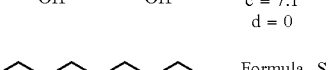 | Formula (7) e = 4.4 | Same as R² | Same as R¹ | 2352 | (3Y) |
| Comparative Example 7 | 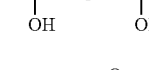 | Formula (6) c = 4.5 d = 4.5 | — | — | 1264 | (1Z) |

In addition, the number average molecular weights (Mn) of the compounds of Examples 1 to 38 and Comparative Examples 1 to 7 were obtained by the above-described $^1$H-NMR and $^{19}$F-NMR measurement. The results are shown in Tables 1 to 7. It is inferred that, in the values of the average molecular weight of the synthesized compounds, variations of approximately 1 to 5 may exist depending on, for example, the molecular weight distributions of the fluoropolyether used as a raw material of the compounds and differences in the operation at the time of synthesizing the compounds.

Next, solutions for forming a lubricating layer were prepared using the compounds obtained in Examples 1 to 38 and Comparative Examples 1 to 7 by a method shown below. Moreover, lubricating layers of magnetic recording media were formed using the obtained solutions for forming a lubricating layer by a method shown below, and magnetic recording media of Examples 1 to 38 and Comparative Examples 1 to 7 were obtained.

"Solutions for Forming Lubricating Layer"

The compounds obtained in Examples 1 to 38 and Comparative Examples 1 to 7 were each dissolved in VERTREL (registered trademark) XF (trade name, manufactured by Dupont-Mitsui Fluorochemicals Co., Ltd.), which is a fluorine-based solvent, diluted with VERTREL XF such that the film thicknesses of the coating films became 9 Å to 10 Å when applied onto protective layers, and used as solutions for forming a lubricating layer.

"Magnetic Recording Media"

Magnetic recording media each having an adhesive layer, a soft magnetic layer, a first underlayer, a second underlayer, a magnetic layer, and a protective layer sequentially provided on a substrate having a diameter of 65 mm were prepared. As the protective layer, a carbon layer with a thickness of 1 to 5 nm was used. The solutions for forming a lubricating layer of Examples 1 to 38 and Comparative Examples 1 to 7 were each applied onto the protective layers of the magnetic recording media, in which the individual layers up to the protective layer had been formed, by the dipping method. The dipping method was carried out under conditions of an immersion speed of 10 mm/sec, an immersion time of 30 seconds and a lifting speed of 1.2 mm/sec.

Thereafter, a burnishing step was performed in which burnishing tape holding abrasive grains having a grain size #6000 was scanned on the surface of each of the magnetic recording media on which the lubricating layer was formed.

The magnetic recording media after the burnishing step were placed in a thermostatic chamber at 120° C. to perform a heat treatment for 10 minutes.

Magnetic recording media (which were burnished) of Examples 1 to 38 and Comparative Examples 1 to 7 were obtained through the above-described steps.

In addition, magnetic recording media (which were unburnished) of Examples 1 to 38 and Comparative Examples 1 to 7 were obtained in the same manner as the burnished magnetic recording media except that a burnishing step was not performed.

(Film Thickness Measurement)

The film thicknesses of the lubricating layers in the magnetic recording media (which were burnished and unburnished) of Examples 1 to 38 and Comparative Examples 1 to 7 thus obtained were measured using FT-IR (trade name: Nicolet iS50, manufactured by Thermo Fisher Scientific Inc.). In all of the magnetic recording media of Examples 1 to 38 and Comparative Examples 1 to 7, there was no difference in the film thickness of the lubricating layer between being burnished and being unburnished. The results are shown in Tables 8 to 11.

TABLE 8

| | Compound | Film thickness (Å) | Unburnished | Burnished |
|---|---|---|---|---|
| Example 1 | (1A) | 9.0 | A | B |
| Example 2 | (1B) | 9.0 | A | A |
| Example 3 | (1C) | 9.0 | A | A |
| Example 4 | (1D) | 9.0 | B | B |
| Example 5 | (1E) | 9.0 | A | B |
| Example 6 | (1F) | 9.0 | A | B |
| Example 7 | (1G) | 9.0 | A | B |
| Example 8 | (1H) | 9.0 | A | A |
| Example 9 | (1I) | 9.0 | A | A |
| Example 10 | (1J) | 9.0 | A | B |
| Example 11 | (1K) | 9.0 | A | A |
| Example 12 | (1L) | 9.0 | A | B |
| Example 13 | (1M) | 9.0 | A | A |

TABLE 9

| | Compound | Film thickness (Å) | Unburnished | Burnished |
|---|---|---|---|---|
| Example 14 | (2A) | 9.0 | A | B |
| Example 15 | (2B) | 9.0 | A | A |
| Example 16 | (2C) | 9.0 | A | A |
| Example 17 | (2D) | 9.0 | B | B |
| Example 18 | (2E) | 9.0 | A | B |
| Example 19 | (2F) | 9.0 | A | B |
| Example 20 | (2G) | 9.0 | A | B |
| Example 21 | (2H) | 9.0 | A | A |
| Example 22 | (2I) | 9.0 | A | A |
| Example 23 | (2J) | 9.0 | A | B |
| Example 24 | (2K) | 9.0 | A | B |
| Example 25 | (2L) | 9.0 | A | B |

TABLE 10

| | Compound | Film thickness (Å) | Unburnished | Burnished |
|---|---|---|---|---|
| Example 26 | (3A) | 9.0 | A | B |
| Example 27 | (3B) | 9.0 | A | A |
| Example 28 | (3C) | 9.0 | A | A |
| Example 29 | (3D) | 9.0 | B | B |
| Example 30 | (3E) | 9.0 | A | B |
| Example 31 | (3F) | 9.0 | A | B |
| Example 32 | (3G) | 9.0 | A | B |
| Example 33 | (3H) | 9.0 | A | A |
| Example 34 | (3I) | 9.0 | A | A |
| Example 35 | (3J) | 9.0 | A | B |
| Example 36 | (3K) | 9.0 | A | A |
| Example 37 | (3L) | 9.0 | A | B |
| Example 38 | (4A) | 9.0 | A | B |

TABLE 11

| | Compound | Film thickness (Å) | Unburnished | Burnished |
|---|---|---|---|---|
| Comparative Example 1 | (1X) | 9.0 | E | E |
| Comparative Example 2 | (2X) | 9.0 | E | E |
| Comparative Example 3 | (3X) | 9.0 | E | E |
| Comparative Example 4 | (1Y) | 9.0 | E | E |
| Comparative Example 5 | (2Y) | 9.0 | E | E |
| Comparative Example 6 | (3Y) | 9.0 | E | E |
| Comparative Example 7 | (1Z) | 9.0 | E | E |

Next, corrosion resistance tests shown below were performed on the burnished and unburnished magnetic recording media of Examples 1 to 38 and Comparative Examples 1 to 7.

(Corrosion Resistance Tests)

The magnetic recording media were exposed to conditions of 85° C. and a relative humidity of 90% for 48 hours. Thereafter, number of corroded spots of the magnetic recording media was counted using an optical surface analyzer and evaluated based on the following evaluation criteria. The results are shown in Tables 8 to 11.

"Evaluation Criteria"

A: Less than 200
B: Greater than or equal to 200 and less than 400.
C: Greater than or equal to 400 and less than 600.
D: Greater than or equal to 600 and less than 800.
E: Greater than or equal to 800

As shown in Tables 8 to 10, the results of the corrosion resistance tests for the magnetic recording media of Examples 1 to 38 having a lubricating layer containing the compound represented by Formula (1) in both cases where the magnetic recording media were subjected to and not subjected to tape burnishing were A or B, which showed favorable corrosion resistance.

On the other hand, as shown in Table 11, the results of the corrosion resistance tests for the magnetic recording media of Comparative Examples 1 to 7 in both cases where the magnetic recording media were subjected to and not subjected to tape burnishing were all E, which showed inferior corrosion resistance compared to the magnetic recording media of Examples 1 to 38.

More specifically, the magnetic recording media having a lubricating layer containing a compound in which the number of carbon atoms in the linking group between the carbon atom to which the terminal hydroxyl group is bound and the carbon atom to which the adjacent hydroxyl group is bound is 1 to 4 showed excellent corrosion resistance in contrast to the magnetic recording media having a lubricating layer containing a compound in which the number of carbon atoms in the above-described linking group is 0 (Examples 7 to 9 in contrast to Comparative Example 1, Examples 20 to 22 in contrast to Comparative Example 2, Examples 32 to 34 in contrast to Comparative Example 3, Example 10 in contrast to Comparative Example 4, Example 23 in contrast to Comparative Example 5, and Example 35 in contrast to Comparative Example 6). In particular, the magnetic recording media having a lubricating layer containing a compound having more carbon atoms of the above-described linking group (Examples 8 and 9, Examples 21 and 22, and Examples 33 and 34) had favorable corrosion resistance. It is inferred that this is because increasing the number of carbon atoms in the above-described linking group may increase the hydrophobicity of the lubricating layer, thereby preventing water from intruding below the lubricating layer.

In addition, even in the magnetic recording media having a lubricating layer containing a compound in which the linking group between the carbon atom to which the terminal hydroxyl group is bound and the carbon atom to which the adjacent hydroxyl group is bound have an oxygen atom, excellent corrosion resistance was obtained (Examples 1 to 6, Examples 11 to 19, Examples 24 to 31, and Examples 36 to 38) compared to the magnetic recording media having a lubricating layer containing a compound in which the carbon atom to which the terminal hydroxyl group is bound and the carbon atom to which the adjacent hydroxyl group is bound are bound to each other (Comparative Examples 1 to 6). It is inferred that this is because even if the above-described linking group has an oxygen atom, the number of carbon atoms contained in the linking group is within an appropriate range, so that the lubricating layer exhibits appropriate hydrophobicity and intrusion of water can be prevented by the lubricating layer.

In addition, those in which the total number of hydroxyl groups in $R^1$ and hydroxyl groups in $R^4$ in Formula (1) is 4 (For example, Examples 2, 3, 8, and 9) had particularly favorable corrosion resistance. It is inferred that this is because, in the case where the total number of hydroxyl groups in $R^1$ and hydroxyl groups in $R^4$ is 4, the interaction between the hydroxyl groups is not excessive, intramolecular aggregation is unlikely to occur, and a lubricating layer which is likely to adhere closely to a protective layer and has an appropriate coating rate can be obtained compared to a case where the above-described total number is 6. In addition, it is inferred that this is because, in the case where the total number of hydroxyl groups in $R^1$ and hydroxyl groups in $R^4$ is 4, the hydrophilicity of a molecule is not too high, and a lubricating layer having appropriate hydrophobicity can be obtained compared to the case where the above-described total number is 6.

In addition, the magnetic recording media of Examples 1 to 38 exhibited excellent corrosion resistance in contrast to the magnetic recording medium of Comparative Example 7. Water resistance is imparted to the lubricating layer due to low surface energy of PFPE chains. In Examples 1 to 38 in which compounds having two PFPE chains are used, the proportion of the PFPE chains in a molecule of the compounds is high compared to Comparative Example 7 in which a compound having one PFPE chain is used. For this reason, it is inferred that, in the magnetic recording media of Examples 1 to 38, the lubricating layer has favorable water resistance and the intrusion of water can be prevented by the lubricating layer compared to the magnetic recording medium of Comparative Example 7.

INDUSTRIAL APPLICABILITY

By using the lubricant for a magnetic recording medium containing the fluorine-containing ether compound of the present invention, a lubricating layer highly effective in suppressing corrosion of a magnetic recording medium can be formed.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by Formula (1) below,

(in Formula (1), $R^2$ and $R^3$ consist of perfluoropolyether chains; and —$CH_2$—$R^1$ and —$CH_2$—$R^4$ are represented by Formula (2) below),

in Formula (2), [A] is represented by Formula (3) below, [B] is represented by Formula (4) below, Z is H or a group represented by Formula (5) below; [A] and [B] in Formula (2) may be exchanged with each other, and Z is the group represented by Formula (5) below in a case where [A] is directly bound to —OZ, and

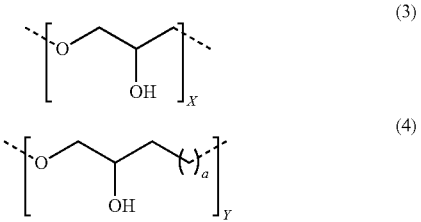

(3)

(4)

in Formula (3), X is an integer of 0 to 2, in Formula (4), Y is an integer of 0 to 1 and a is an integer of 1 to 4; the sum of X in Formula (3) and Y in Formula (4) is 1 or 2; and b in Formula (5) is an integer of 2 to 4.

2. The fluorine-containing ether compound according to claim 1, wherein $R^2$ and $R^3$ in Formula (1) above are any of Formulae (6) to (8) below,

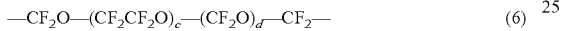

(6)

(in Formula (6), c and d indicate an average degree of polymerization and each represent 0 to 20, provided that c or d is 0.1 or more),

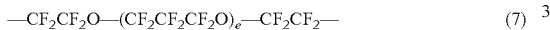

(7)

(in Formula (7), e indicates an average degree of polymerization and represents 0.1 to 20), and

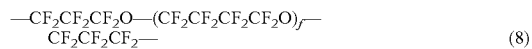

(8)

(in Formula (8), f indicates an average degree of polymerization and represents 0.1 to 10).

3. The fluorine-containing ether compound according to claim 1, wherein $R^1$ and $R^4$ in Formula (1) above each have two polar groups.

4. The fluorine-containing ether compound according to claim 1, wherein $R^1$ and $R^4$ in Formula (1) above are the same as each other.

5. The fluorine-containing ether compound according to claim 1, wherein $R^2$ and $R^3$ in Formula (1) above are the same as each other.

6. The fluorine-containing ether compound according to claim 1, wherein a number average molecular weight thereof is within a range of 500 to 10,000.

7. A lubricant for a magnetic recording medium comprising:
the fluorine-containing ether compound according to claim 1.

8. A magnetic recording medium,
wherein at least a magnetic layer, a protective layer, and a lubricating layer are sequentially provided on a substrate, and
wherein the lubricating layer contains the fluorine-containing ether compound according to claim 1.

9. The magnetic recording medium according to claim 8, wherein an average film thickness of the lubricating layer is 0.5 nm to 2.0 nm.

10. The fluorine-containing ether compound according to claim 1, wherein the number of polar groups in $R^1$ is the same as the number of polar groups in $R^4$.

* * * * *